US012740981B2

(12) United States Patent
Lerario et al.

(10) Patent No.: US 12,740,981 B2
(45) Date of Patent: Sep. 22, 2026

(54) COMPOSITIONS AND METHODS FOR TREATING CANCER

(71) Applicant: The Regents of the University of Michigan, Ann Arbor, MI (US)

(72) Inventors: Antonio M. Lerario, Ann Arbor, MI (US); Dipika Mohan, Ann Arbor, MI (US); Gary Hammer, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1137 days.

(21) Appl. No.: 17/617,546

(22) PCT Filed: Jun. 10, 2020

(86) PCT No.: PCT/US2020/037039

§ 371 (c)(1),
(2) Date: Dec. 8, 2021

(87) PCT Pub. No.: WO2020/252054

PCT Pub. Date: Dec. 17, 2020

(65) Prior Publication Data

US 2022/0241276 A1 Aug. 4, 2022

Related U.S. Application Data

(60) Provisional application No. 62/882,147, filed on Aug. 2, 2019, provisional application No. 62/859,933, filed on Jun. 11, 2019.

(51) Int. Cl.

| | |
|---|---|
| ***A61K 31/4985*** | (2006.01) |
| ***A61K 45/06*** | (2006.01) |
| ***A61P 35/00*** | (2006.01) |
| ***C12Q 1/6886*** | (2018.01) |
| ***G01N 33/50*** | (2006.01) |
| ***G01N 33/575*** | (2026.01) |
| ***G01N 33/57525*** | (2026.01) |

(52) U.S. Cl.

CPC .......... *A61K 31/4985* (2013.01); *A61K 45/06* (2013.01); *A61P 35/00* (2018.01); *C12Q 1/6886* (2013.01); *G01N 33/5011* (2013.01); *G01N 33/575* (2026.01)

(58) Field of Classification Search

CPC ..... A61K 31/4985; A61K 45/06; A61P 35/00; C12Q 1/6886; C12Q 2600/106; C12Q 2600/154; C12Q 2600/158; G01N 33/5011; G01N 33/574; G01N 33/57438; G01N 2800/52; G01N 33/5041

See application file for complete search history.

(56) References Cited

U.S. PATENT DOCUMENTS

| | | | |
|---|---|---|---|
| 8,084,599 | B2 | 12/2011 | Rossi et al. |
| 9,457,081 | B2 | 10/2016 | Lee et al. |
| 10,066,270 | B2 | 9/2018 | Bussey et al. |
| 2014/0045915 | A1 | 2/2014 | Skog et al. |
| 2015/0119350 | A1 | 4/2015 | Kebebew et al. |
| 2015/0291954 | A1 | 10/2015 | Bettencourt et al. |
| 2016/0153053 | A1 | 6/2016 | Skog et al. |
| 2018/0221350 | A1 | 8/2018 | Kc et al. |
| 2022/0241276 | A1 | 8/2022 | Lerario et al. |

FOREIGN PATENT DOCUMENTS

| | | |
|---|---|---|
| WO | WO 2013/142214 | 9/2013 |
| WO | WO 2016/064716 | 4/2016 |
| WO | WO 2019/108568 | 6/2019 |
| WO | WO 2020/252054 | 12/2020 |

OTHER PUBLICATIONS

Fassnacht M et al. Linsitinib (OSI-906) versus placebo for patients with locally advanced or metastatic adrenocortical carcinoma: a double-blind, randomised, phase 3 study. Lancet Oncol. Apr. 2015;16(4):426-35. doi: 10.1016/S1470-2045(15)70081-1. Epub Mar. 18, 2015. PMID: 25795408. (Year: 2015).*

Zheng et al. Comprehensive Pan-Genomic Characterization of Adrenocortical Carcinoma. Cancer Cell. May 9, 2016;29(5):723-736. doi: 10.1016/j.ccell.2016.04.002. Erratum in: Cancer Cell. Aug. 8, 2016;30(2):363. doi: 10.1016/j.ccell.2016.07.013. PMID: 27165744; PMCID: PMC4864952. (Year: 2016).*

Zheng et al. Comprehensive Pan-Genomic Characterization of Adrenocortical Carcinoma. Cancer Cell. May 9, 2016. 29(5); 723-736.

Office Action for CN 201880088075.6, mailed Feb. 5, 2023, 9 pages. With English translation.

Haluska et'al: "Safety, 1-15 tolerability, and pharmacokinetics of the anti-IGF-1R monoclonal antibody figitumumab in patients with refractory adrenocortical carcinoma", Cancer Chemotherapy and Pharmacology, Springer, Berlin, DE, vol. 65, No. 4, Aug. 2, 2009, pp. 765-773.

Lerario A.M. et al: "The Combination of Insulin-Like Growth Factor Receptor 1 (IGF1R) Antibody Cixutumumab and Mitotane as a First-Line Therapy-for Patients with Recurrent/Metastatic Adrenocortical Carcinoma: a Multi-institutional NCI-Sponsored Triel", Hormones and Cancer, vol. 5, No. 4, Sep. 6, 2014 (Sep. 6, 2014), pp. 232-239.

(Continued)

*Primary Examiner* — Bruck Kifle
*Assistant Examiner* — Kevin S Martin
(74) *Attorney, Agent, or Firm* — Casimir Jones, S.C.; Tanya A. Arenson

(57) ABSTRACT

The present disclosure relates to compositions, systems, and methods for treating cancer. In particular, the present disclosure relates to compositions, systems, and methods for utilizing gene expression and methylation profiles to stratify and treat adrenocortical carcinoma and drugs which have utility for patients stratified by these means.

5 Claims, 8 Drawing Sheets

(56) References Cited

OTHER PUBLICATIONS

Extended European Search Report for EP 20821939.4 mailed Aug. 28, 2023, 9 pages.

Ardolino L. et al. Advanced Adrenocortical Carcinoma (ACC): a Review with Focus on Second-Line Therapies, Hormones and Cancer, vol. 11, No. 3-4, Aug. 2020 (Aug. 2020), pp. 155-169.

Cheng X. et al. Therapeutic potential of targeting the Wnt/[beta]—catenin signaling pathway in colorectal cancer, Biomedicine & Pharmacotherapy, vol. 110, Feb. 1, 2019 (Feb. 1, 2019), pp. 473-481.

Jung, Y. et al. Wnt signaling in cancer: therapeutic targeting of Wnt signaling beyond [beta]-catenin and the destruction complex, Experimental and Molecular Medicine, vol. 52, No. 2, Feb. 1, 2020 (Feb. 1, 2020), pp. 183-191.

Tissier F. et al. Mutations of [beta]-Catenin in Adrenocortical Tumors: Activation of the Wnt Signaling Pathway is a Frequent Event in both Benign and Malignant Adrenocortical Tumors, Cancer Research, vol. 65, No. 17, Sep. 1, 2005 (Sep. 1, 2005), pp. 7622-7627, XP093204321, San Diego, CA . Philadelphia. Retrieved from the Internet: <URL:https://watermark.silverchair.com/7622-7627.pdf?token=AQECAHi208BE49Ooan9kkhW_Ercy7Dm3ZL9Cf3qfKAc485ysgAAA2QWggNgBgkqhkiG9w0BBwagggNRMIIDTQIBADCCA0YGCSGGSlb3DQEHATAeBglghkgBZQMEAS4wEQQMfgxdpSzh01CtBqGqAgEQglIDF4banirLqQuTkXCZSg_iVDgj0 KgR-rERK710j_S7QLbwsoX5gcFlisn9gVosmaPj9qMKIC132zny57CeMgFiu5E>.

Tingting G. et al. Progress in Research of Bispecific Antibody Drugs. Chinese Journal of New Drugs, 25(5), Dec. 31, 2016; 518-523.

Berruti et al. Adjuvant therapy in patients with adrenocortical carcinoma: a position of an international panel. J Clin Oncology. Jun. 21, 2010, 28(23):e401-2.

Beuschlein, et al. Major prognostic role of Ki67 in localized adrenocortical carcinoma after complete resection. J Clin Endocrinol Metab. Mar. 2015;100(3):841-9.

De Rynies et al. Gene expression profiling reveals a new classification of adrenocortical tumors and identifies molecular predictors of malignancy and survival. J Clin Oncol. Mar. 1, 2009;27(7):1108-15.

Eisenhauer et al. Clinical benefit in oncology trials: is this a patient-centred or tumour-centred end-point? Eur J Cancer. Sep. 2009;45(13):2249-52.

Extended European Search Report for EP 18882759.6, mailed Jul. 28, 2021, 9 pages.

Fassnacht et al. Linsitinib (OSI-906) versus placebo for patients with locally advanced or metastatic adrenocortical carcinoma: a double-blind, randomised, phase 3 study. Lancet Oncol. Apr. 2015;16(4):426-35.

Fragoso, M.C.B.V. et al. Combined expression of BUB1B, DLGAP5, and PINK1 as predictors of poor outcome in adrenocortical tumors: validation in a Brazilian cohort of adult and pediatric patients. Eur J Endocrinol. Jan. 2012;166(1):61-7.

Hanzelmann, et al. GSVA: gene set variation analysis for microarray and RNA-seq data. BMC Bioinformatics. Jan. 16, 2013;14:7.

International Search Report and Written Opinion for PCT/US2018/062709, mailed Feb. 19, 2019, 17 pages.

International Search Report and Written Opinion for PCT/US2020/37039, mailed Sep. 14, 2020, 21 pages.

Lerario et al. Genetics and epigenetics of adrenocortical tumors. Mol Cell Endocrinol. Apr. 5, 2014;386(1-2):67-84.

Mohan et al. Therapeautic Targets for Adrenocortical Carcinoma in the Genomics Era. J. Endocrine Soc. Sep. 26, 2018, 2(11); 1259-74.

Mohan et al., Targeted Assessment of G0S2 Methylation Identifies a Rapidly Recurrent, Routinely Fatal Molecular Subtype of Adrenocortical Carcinoma. Clin Cancer Res. Jun. 1, 2019;25(11):3276-3288.

Office Action for CN 201880088075.6, mailed Jul. 18, 2022, 6 pages. With English translation.

Office Action for JP 2020-529263 mailed Jul. 5, 2022, 3 pages. With English translation.

Weiss et al. Pathologic features of prognostic significance in adrenocortical carcinoma. Am J Surg Pathol. Mar. 1989;13(3):202-6.

Zheng et al. Comprehensive Pan-Genomic Characterization of Adrenocortical Carcinoma. Cancer Cell. Aug. 8, 2016;30(2):363.

Anwar et al. p38-mediated phosphorylation at T367 induces EZH2 cytoplasmic localization to promote breast cancer metastasis. Nat Commun. Jul. 18, 2018;9(1):2801.

Bassett et al. The orphan nuclear receptors NURR1 and NGFIB regulate adrenal aldosterone production. Mol Endocrinol. Feb. 2004;18(2):279-90.

Borges et al. Wnt/β-catenin activation cooperates with loss of p53 to cause adrenocortical carcinoma in mice. Oncogene. Jul. 2020;39(30):5282-5291.

Crona et al. RNA-Sequencing Analysis of Adrenocortical Carcinoma, Pheochromocytoma and Paraganglioma from a Pan-Cancer Perspective. Cancers (Basel). Dec. 15, 2018;10(12):518.

Grisanti et al. Are we failing in treatment of adrenocortical carcinoma? Lights and shadows of molecular signatures. Curr Opin Endocr Metab Res. Oct. 8, 2019;8:80-87.

Hadjidemetriou. Identification of DLK1-positive cell clusters in the human adrenal cortex and their potential involvement in adrenocortical carcinoma. Queen Mary University of London. 2019 (Apr. 23, 2019).

Hnisz et al., Convergence of Developmental and Oncogenic Signaling Pathways at Transcriptional Super-Enhancers. Mol. Cel. vol. 58, Issue 2, Apr. 16, 2015, pp. 362-370.

Hnisz et al., Super-enhancers in the control of cell identity and disease. Cell. Nov. 7, 2013;155(4):934-47.

Hoffmeyer et al. Trimethylation and Acetylation of β-Catenin at Lysine 49 Represent Key Elements in ESC Pluripotency. Cell Rep. Mar. 21, 2017;18(12):2815-2824.

Kagey et al. Mediator and cohesin connect gene expression and chromatin architecture. Nature. Sep. 23, 2010;467(7314):430-5.

Kahn, Can we safely target the WNT pathway? Nat Rev Drug Discov. Jul. 2014;13(7):513-32.

Kim et al. Targeted disruption of beta-catenin in Sf1-expressing cells impairs development and maintenance of the adrenal cortex. Development. Aug. 2008;135(15):2593-602.

Kim et al., Synthetic dsRNA Dicer substrates enhance RNAi potency and efficacy. Nat Biotechnol. Feb. 2005;23(2):222-6.

Loven et al., Selective Inhibition of Tumor Oncogenes by Disruption of Super-Enhancers. Cell, 153 (2). pp. 320-334.

Madoux et al., Potent, selective and cell penetrant inhibitors of SF-1 by functional ultra-high-throughput screening. Mol Pharmacol. Jun. 2008;73(6):1776-84.

Mathieu et al. Steroidogenic differentiation and PKA signaling are programmed by histone methyltransferase EZH2 in the adrenal cortex. Proc Natl Acad Sci USA. Dec. 26, 2018;115(52):E12265-E12274.

Merika et al. Recruitment of CBP/p300 by the IFN beta enhanceosome is required for synergistic activation of transcription. Mol Cell. Jan. 1998;1(2):277-87.

Mizusaki et al. Dax-1 (dosage-sensitive sex reversal-adrenal hypoplasia congenita critical region on the X chromosome, gene 1) gene transcription is regulated by wnt4 in the female developing gonad. Mol Endocrinol. Apr. 2003;17(4):507-19.

Mohan et al. New strategies for applying targeted therapies to adrenocortical carcinoma. Curr Opin Endocr Metab Res. Oct. 2019; 8: 72-79.

Pott et al. What are super-enhancers? Nat Genet. Jan. 2015;47(1):8-12.

Raisner et al., Enhancer Activity Requires CBP/P300 Bromodomain-Dependent Histone H3K27 Acetylation. Cell. vol. 24, Issue 7, Aug. 14, 2018, pp. 1722-1729.

Rose et al., Functional polarity is introduced by Dicer processing of short substrate RNAs. Nucleic Acids Res. Jul. 26, 2005;33(13):4140-56.

Sabari et al. Coactivator condensation at super-enhancers links phase separation and gene control. Science. Jul. 27, 2018;361(6400):eaar3958.

(56) References Cited

OTHER PUBLICATIONS

Shi et al., Role of SWI/SNF in acute leukemia maintenance and enhancer-mediated Myc regulation. Genes Dev. Dec. 15, 2013; 27(24): 2648-2662.
Whyte et al. Master transcription factors and mediator establish super-enhancers at key cell identity genes. Cell. Apr. 11, 2013;153(2):307-19.
Zamudio et al., Lineage-specific evolution and gene flow in Listeria monocytogenes are independent of bacteriophages. Environ Microbiol. Dec. 2020;22(12):5058-5072.
Zhu et al. Inc-β-Catm elicits EZH2-dependent β-catenin stabilization and sustains liver CSC self-renewal. Nat Struct Mol Biol. Jul. 2016;23(7):631-9.

* cited by examiner

Cell cycle # of patients

Figure 2:
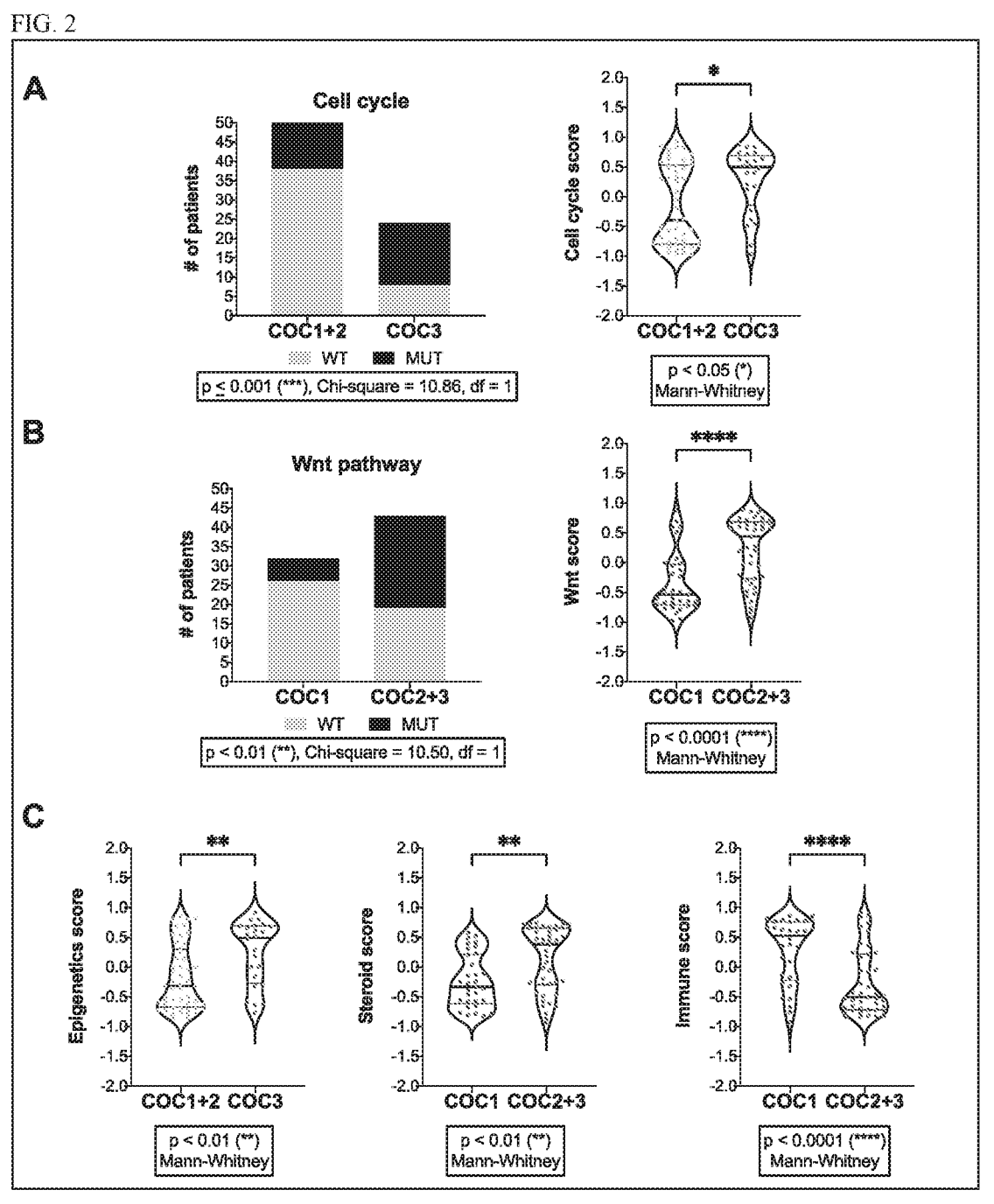

COC1+2 COC3

WT MUT p ≤ 0.001 (***), Chi-square = 10.86, df = 1

Cell cycle score

COC1+2 COC3 p < 0.05 (*) Mann-Whitney

B

Wnt pathway # of patients

COC1 COC2+3

WT MUT p < 0.01 (**), Chi-square = 10.50, df = 1

Wnt score

COC1 COC2+3 p < 0.0001 (****) Mann-Whitney

C

Epigenetics score

COC1+2 COC3 p < 0.01 (**) Mann-Whitney

Steroid score

COC1 COC2+3 p < 0.01 (**) Mann-Whitney

Immune score

COC1 COC2+3 p < 0.0001 (****) Mann-Whitney

FIG. 6

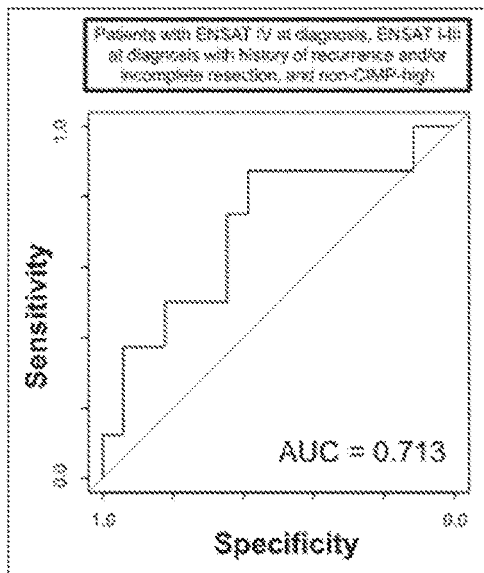

| Resampling parameters and results | |
|---|---|
| Cross-validated (5 fold, repeated 20 times) | |
| N (total # of samples) | 25 |
| Accuracy | 0.709 |
| Kappa | 0.2401505 |
| | |
| Confusion matrix and performance on dataset at optimal cutoff | |
| *BUB1B-PINK1* z-score cutoff | 0.596742 |
| | |
| Sensitivity | 0.875 |
| Specificity | 0.5556 |
| Positive Predictive Value | 0.5 |
| Negative Predictive Value | 0.9091 |

NOTE. Optimal cutoff was chosen to maximize negative predictive value to exclude COC2-3.

FIG. 7

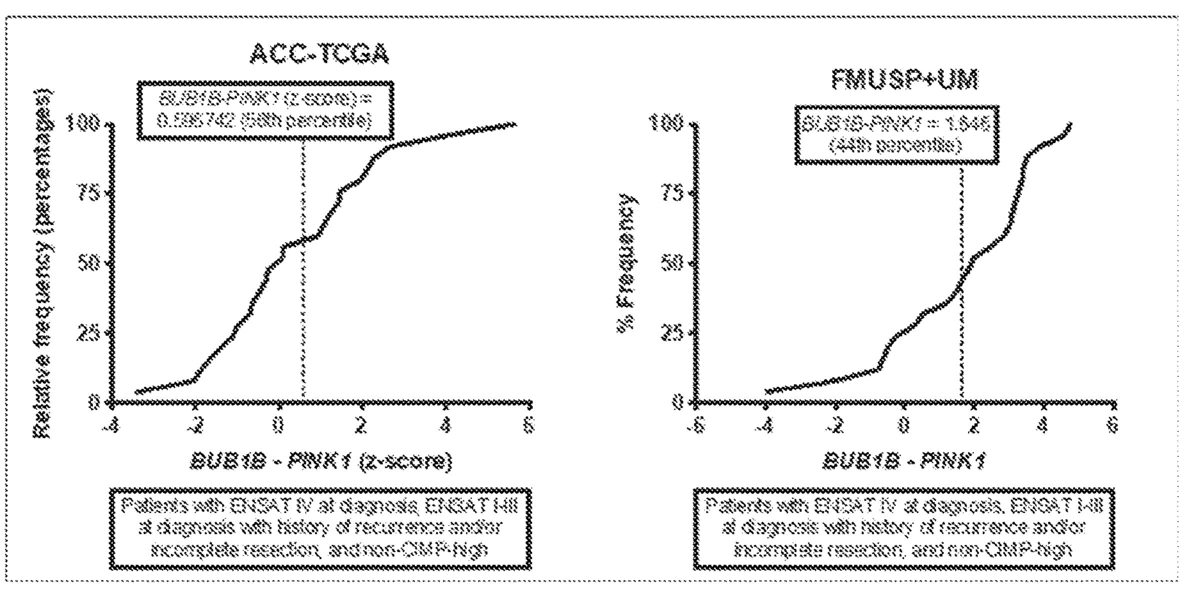

COMPOSITIONS AND METHODS FOR TREATING CANCER

CROSS REFERENCE TO RELATED APPLICATION

This application is a 371 U.S. National Phase Entry of pending International Application No. PCT/US2020/037039, filed Jun. 10, 2020, which claims priority to and the benefit of U.S. Provisional Application No. 62/859,933, filed Jun. 11, 2019, and U.S. Provisional Application No. 62/882,147, filed Aug. 2, 2019, the contents of which are hereby incorporated by reference in their entireties.

FIELD OF THE DISCLOSURE

The present disclosure relates to compositions, systems, and methods for treating cancer. In particular, the present disclosure relates to compositions, systems, and methods for utilizing gene expression and methylation profiles to stratify and treat adrenocortical carcinoma and drugs which have utility for patients stratified by these means.

BACKGROUND OF THE DISCLOSURE

Adrenocortical carcinoma (ACC) is a rare malignancy with an overall dismal prognosis. Treatment options for ACC are limited, and surgery is the only therapy that can provide long-term remission and cure. Despite surgery, many patients with early-stage disease develop metastases post-operatively and therefore require systemic treatment. For this reason, following margin-free surgical resection, adjuvant therapy with the adrenolytic compound mitotane is now part of the standard care for most ACC patients; however, current pharmacologic treatment options are highly limited and leave a major unmet medical need for additional options. Recent studies confirm that mitotane is only marginally effective while highly toxic. Therapeutic serum levels of mitotane typically take several months of drug administration to achieve, and up to 90% of patients will inevitably recur during adjuvant mitotane therapy after surgery or progress during mitotane therapy for non-resectable disease (either during or following this dosage escalation window). Furthermore, the efficacy of cytotoxic chemotherapy for nonresectable disease is similarly limited and side effects are significant. As a result, there is a critical unmet medical need for new therapies which are safer, more effective, or both, than current options for patients.

Current approaches to patient stratification rely on histological assessment of cell proliferation. The gold standard K167 index or mitotic counts have several limitations and do not reliably identify patients who might respond to a specific treatment. Improved methods for identifying patients who might respond to a specific treatment are needed.

SUMMARY OF THE DISCLOSURE

The present disclosure relates to compositions, systems, and methods for treating cancer. In particular, the present disclosure relates to compositions, systems, and methods for utilizing gene expression and methylation profiles to stratify and treat adrenocortical carcinoma, and, to drugs which have utility for patients stratified by these means.

During development of embodiments of the present disclosure, compositions and methods for identifying a patient population amenable to treatment with IGF1R inhibitors (e.g., linsitinib) were developed. In particular, in Mohan & Lerario et al. Clinical Cancer Research 2019, it was observed that G0S2 methylation is prevalent in the primary tumors of 54% of patients with metastatic disease. Higher BUB1B-PINK1 predicts slower disease course even in patients with metastatic disease (Table 4). Together with G0S2 methylation, BUB1B-PINK1 expression score is additionally used, specifically to exclude patients with a "low" BUB1B-PINK1, with the goal of identifying a non-obvious and previously not identifiable subpopulation of patients predicted to be unusually responsive to treatment with an IGF1R inhibitor. To delineate this specific population, and because a split was observed in the survival curves of the placebo/treatment arms of a previously conducted linsitinib clinical trial at the 25% survival fraction (FIG. 9 and Example 2), a cutoff of BUB1B-PINK1 at the 44th percentile of non-CIMP-high patients with a history of metastatic disease is used, to further define patients in this unusually responsive subpopulation. This results in the inclusion of 56% of patients with non-CIMP-high metastatic disease, and yields, after the application of these collective steps, a subpopulation comprising (0.56)(1−0.54)=25.8% of all patients with metastatic disease, mirroring the cohort of patients in the 25% survival fraction identified in FIG. 9. A beneficial feature of this cutoff is that it optimizes the identification of patients with chromosomal tumors possessing recurrent alterations leading to upregulation of IGF2 and infrequently possessing other recurrent somatic alterations from ACC-TCGA (COC1; FIGS. 1, 2, 3), reconciling the biological motivation for the use of targeted therapies described herein.

Accordingly, the compositions and methods described herein provide improved patient care by customizing therapy for ACC to a particular subtype of ACC and improving the efficacy of IGF1R inhibitor therapy by providing such therapy only to patients identified as likely to respond.

For example, in some embodiments, provided herein is a method for treating adrenocortical carcinoma (ACC), comprising: administering an agent that blocks IGF1R signaling (e.g., an IGF1R inhibitor such as linsitinib) to a subject identified as having cluster 1 (COC1) ACC. In some embodiments, the subject is identified as having COC1 ACC by measuring the level of G0S2 methylation and a level of expression of BUB1B and PINK1. For example, in some embodiments, a G0S2 methylation level below a threshold level (e.g., less than 4.696% methylation, for example as determined by methylation sensitive restriction digest/amplification) and a BUB1B-PINK1 expression score above a threshold level cutoff of BUB1B-PINK1 is indicative of COC1 ACC. In some embodiments, the threshold level of G0S2 methylation is determined using unsupervised complete hierarchical clustering using Euclidean distance on logit-transformed methylation beta-values. In some embodiments, linsinitib is administered as a monotherapy.

The present disclosure is not limited to particular threshold levels for BUB1B-PINK1 expression scores. In some embodiments, the threshold level is the 44th percentile (e.g., plus or minus 1, 2, 3, 4, 5, 6, 7, 8, 9, or 10 percentiles) of ACC samples with a history of metastatic disease having a G0S2 methylation level below a threshold level (e.g., less than 4.696% methylation, for example as determined by methylation sensitive restriction). In some specific embodiments, the threshold level of BUB1B-PINK1 expression is 1.4, 1.5, 1.6, 1.7, or higher, for example as determined by subtracting the copy threshold values of BUB1B and PINK1 in a sample evaluated using quantitative polymerase chain reaction. In some embodiments, subjects who have a G0S2 methylation level above a threshold level are excluded from treatment with an agent that blocks IGF1R signaling (e.g., IGF1R inhibitor). In some embodiments, subjects who have a G0S2 methylation below a threshold level and a BUB1B-PINK1 expression score below a threshold level are excluded from treatment with an agent that blocks IGF1R signaling (e.g., IGF1R inhibitor).

Additional embodiments provide a method for treating ACC in a subject, comprising: a) identifying the subject as having COC1 ACC by obtaining or having obtained a sample from the subject and measuring the level of G0S2 methylation and a level of expression of BUB1B and PINK1 in the sample; and b) administering an agent that blocks IGF1R signaling (e.g., an IGF1R inhibitor such as linsitinib) to the subject when the subject has a level of G0S2 methylation and a BUB1B-PINK1 expression score indicative of the presence of COC1 ACC.

Other embodiments provide a method for treating ACC in a subject, comprising a) determining the level of G0S2 methylation and a level of expression of BUB1B and PINK1 in a sample from the subject; b) identifying subjects with levels of G0S2 methylation in the sample below a threshold level and a BUB/B-PINK1 expression score above a threshold level as having COC1 ACC; and c) administering an agent that blocks IGF1R signaling (e.g., an IGF1R inhibitor) to the subject identified as having COC1 ACC.

Also provide herein is the use of an agent that blocks IGF1R signaling (e.g., an IGF1R inhibitor) to treat ACC in a subject identified as having COC1 ACC or an agent that blocks IGF1R signaling (e.g., an IGF1R inhibitor) for use in treating ACC in a subject identified as having a COC1 ACC.

Certain embodiments provide a method for treating ACC, comprising: administering an agent that blocks IGF1R signaling (e.g., an IGF1R inhibitor) to a subject identified as having less than a threshold level (e.g., 4.696%) of G0S2 methylation and a BUB1B-PINK1 expression score above a threshold level in a sample isolated from the subject.

In some embodiments, provided herein is a method for treating ACC in a subject, comprising: a) identifying the subject as having a level of G0S2 methylation below a threshold level and a BUB1B PINK1 expression score above a threshold level by obtaining or having obtained a sample from the subject; and measuring the level of G0S2 methylation and a level of expression of BUB1B and PINK1 in the sample; and b) administering an agent that blocks IGF1R signaling (e.g., an IGF1R inhibitor) to the subject when the subject has a level of G0S2 methylation less than a threshold level (e.g., less than 4.696%) and BUB1B PINK1 expression score threshold level.

Yet other embodiments provide a method for treating ACC in a subject, comprising a) determining the level of G0S2 methylation and a level of expression of BUB1B and PINK1 in a sample from the subject; b) identifying subjects with levels of G0S2 methylation in the sample below a threshold level (e.g., less than 4.696%) and a BUB/B-PINK1 expression score above a threshold level; and c) administering an agent that blocks IGF1R signaling (e.g., an IGF1R inhibitor) to subjects identified as having a level of G0S2 methylation below a threshold level (e.g., less than 4.696%) and a BUB1B-PINK1 expression score above a threshold level.

In further embodiments provided is the use of an agent that blocks IGF1R signaling (e.g., an IGF1R inhibitor) to treat ACC in a subject identified as having a level of G0S2 methylation below a threshold level and a BUB1B-PINK1 expression score above a threshold level or an agent that blocks IGF1R signaling (e.g., an IGF1R inhibitor) for use in treating ACC in a subject identified as having a level of G0S2 methylation below a threshold level (e.g., less than 4.696%) and a BUB1B-PINK1 expression score above a threshold level.

Also provided is a method for treating adrenocortical carcinoma (ACC), comprising: a) contacting a sample from a subject diagnosed with ACC with reagents for determining the level of expression of BUB1B, PINK1, and at least one of the level of expression of G0S2 and the methylation status of G0S2; b) characterizing the ACC as molecular subgroup cluster 1 (COC1), cluster 2 (COC2), or cluster 3 (COC3) based on said BUB1B-PINK1 expression score and the level of G0S2 expression or methylation; and c) administering at least one treatment customized for the molecular subgroup to the subject e.g., administering one or more of an inhibitor of a cell cycle effector protein, an inhibitor of a DNA repair protein, a Wnt inhibitor, an NR5A1 inhibitor, or an inhibitor of an epigenetic writer to a subject identified as having a COC3 carcinoma; administering one or more of a Wnt inhibitor or a NR5A1 inhibitor to a subject identified as having COC2 carcinoma; or administering one or more of an agent that blocks IGF1R signaling (e.g., an IGF1R inhibitor) to a subject identified as having a COC1 carcinoma). In some embodiments, the method further comprises administering an agent that blocks IGF1R signaling (e.g., an IGF1R inhibitor) and/or an immune checkpoint inhibitor (in combination with an NR5A1 inhibitor, a glucocorticoid synthesis/metabolism inhibitor or a glucocorticoid receptor inhibitor) to a subject identified as having a COC2 or COC3 carcinoma. In some embodiments, the method further comprises administering an immune checkpoint inhibitor to a subject identified as having COC1.

In some embodiments, the characterizing comprises determining a BUB1B-PINK1 expression score. The present disclosure is not limited to particular cut-off or threshold values for characterizing ACC. For example, in some embodiments, a BUB1B PINK1 expression score above a threshold level and a G0S2 methylation level below a threshold level (e.g., less than 4.696%) is indicative of COC1. In some embodiments, a BUB1B-PINK1 expression score below a threshold level and a G0S2 methylation level below a threshold level (e.g., less than 4.696%) is indicative of COC2. In some embodiments, the presence of greater than 4.696% (e.g., greater than 4.696%, 4.7%, 4.8%, 4.9%, or 5.0%) G0S2 methylation is indicative of COC3. In some embodiments, the BUB1B-PINK1 expression score threshold level is 1.4 to 1.8 (e.g., 1.4, 1.5, 1.6, 1.7, or 1.8). In some embodiments, the BUB1B PINK1 expression score and G0S2 methylation values displayed in Table 1 are utilized to characterize ACC. In some embodiments, the biological sample is a tissue sample, a biopsy sample, a blood sample, or a urine sample. In some embodiments, the reagents are one or more of a nucleic acid probe or probes that hybridizes to at least one of BUB1B. PINK1, and G0S2, one or more nucleic acid primers for the amplification or extension of at least one of BUB1B, PINK1, and G0S2, or one or more nucleic acid primers that bind specifically to methylated G0S2 nucleic acids. In some embodiments, an amplification assay (e.g., real time PCR) is used to measure expression of BUB1B, PINK, and G0S2.

The present disclosure is not limited to particular target genes or therapies. In some embodiments, the therapeutic agent is an antibody, a nucleic acid, or a small molecule. For example, in some embodiments, the cell cycle effector protein is CDK4/6, PLK1, MELK, or AURK and the inhibitor is palbociclib. In some embodiments, the DNA repair protein is WEE1 or PARP and the inhibitor is olaparib or adavosertib. In some embodiments, the epigenetic writer is EZH2 and/or DNMT1 and the inhibitor is 3-deazaneplanocin A, EPZ005687, EPZ-6438 (tazemetostat), decitabine, or 5-Azacytidine. In some embodiments, the IGF1R inhibitor is linsitinib, cixutumumab, ganitumab, figitumumab, dalotuzumab, istiratumab, dusigitumab, or teprotumumab. In some embodiments, the Wnt inhibitor is WNT974 or PRI-724. In some embodiments, the immune checkpoint inhibitor is Ipilimumab, Nivolumab, Pembrolizumab, Atezolizumab, Avelumab, Durvalumab, or Cemiplimab. In some embodiments, the NR5A1 inhibitor is SID 7969543, 45594 [4-(heptyloxy)phenol] or octyloxyphenyl (OOP).

Further embodiments provide a method for characterizing adrenocortical carcinoma (ACC), comprising: a) contacting a sample from a subject diagnosed with ACC with reagents for determining the level of expression of at least one of BUB1B, PINK1, and G0S2 and the methylation status of G0S2; and b) characterizing said ACC as molecular subgroup COC1 when a BUB1B PINK1 expression score above a threshold level and less than a threshold level (e.g., less than 4.696%) G0S2 methylation is identified; characterizing said ACC as COC2 when a BUB1B-PINK1 expression score below a threshold level and less than a threshold level (e.g., 4.696%) G0S2 methylation is identified; and, characterizing said ACC as COC3 when the presence of greater than a threshold level (e.g., 4.696%) G0S2 methylation is identified.

Additional embodiments provide the use of at least one treatment selected from an inhibitor of a cell cycle effector protein, an inhibitor of a DNA repair protein, a Wnt inhibitor, a NR5A1 inhibitor, or epigenetic writer inhibitor to treat ACC in a subject identified as having a COC3 carcinoma; the use of at least one treatment selected from a Wnt inhibitor and a NR5A1 inhibitor to treat ACC in a subject identified as having COC2 carcinoma; or the use of at least one treatment selected from an agent that blocks IGF1R signaling (e.g., an IGF1R inhibitor) and a checkpoint inhibitor to treat ACC in a subject identified as having a COC1 carcinoma.

Yet other embodiments provide at least one treatment selected from an inhibitor of a cell cycle effector protein, an inhibitor of a DNA repair protein, a Wnt inhibitor, a NR5A1 inhibitor, or an epigenetic writer inhibitor for use in treating ACC in a subject identified as having a COC3 carcinoma; at least one treatment selected from a Wnt inhibitor or a NR5A1 inhibitor for use in treating ACC in a subject identified as having COC2 carcinoma; or an agent that blocks IGF1R signaling (e.g., an IGF1R inhibitor) for use in treating ACC in a subject identified as having a COC1 carcinoma.

Certain embodiments provide a method for screening a treatment for adrenocortical carcinoma (ACC), comprising: a) contacting a sample from a subject diagnosed with ACC with reagents for determining the level of expression of at least one of BUB1B, PINK1, and G0S2 and the methylation status of G0S2; b) characterizing said ACC as molecular subgroup COC1, COC2, or COC3 based on said level of expression of BUB1B, PINK1, and G0S2 and methylation status of G0S2; c) administering at least one treatment selected from an inhibitor of a cell cycle effector protein, an inhibitor of a DNA repair protein, a Wnt inhibitor, a NR5A1 inhibitor, or an epigenetic writer inhibitor to a subject identified as having a COC3 carcinoma, administering at least one treatment selected from a Wnt inhibitor or a NR5A1 inhibitor to a subject identified as having COC2 carcinoma, or administering at least one treatment selected from an agent that blocks IGF1R signaling (e.g., an IGF1R inhibitor) and/or a checkpoint inhibitor to a subject identified as having a COC1 carcinoma; and d) assessing the effect of the treatment on one or more signs or symptoms of ACC.

Particular embodiments provide a method for selecting a treatment for adrenocortical carcinoma (ACC), comprising: a) contacting a sample from a subject diagnosed with ACC with reagents for determining the level of expression of at least one of BUB1B, PINK1, and G0S2 and the methylation status of G0S2; b) characterizing said ACC as molecular subgroup COC1, COC2, or COC3 based on said level of expression of BUB1B, PINK1, and G0S2 and methylation status of G0S2; and c) selecting at least one treatment selected from an inhibitor of a cell cycle effector protein, an inhibitor of a DNA repair protein, a Wnt inhibitor, a NR5A1 inhibitor, or an epigenetic writer inhibitor to a subject identified as having a COC3 carcinoma, selecting at least one treatment selected from a Wnt inhibitor and a NR5A1 inhibitor to a subject identified as having COC2 carcinoma, and selecting at least one treatment selected from an agent that blocks IGF1R signaling (e.g., an IGF1R inhibitor) and an immune checkpoint inhibitor to a subject identified as having a COC1 carcinoma.

Additional embodiments will be apparent to persons skilled in the relevant art based on the teachings contained herein.

DESCRIPTION OF THE DRAWINGS

FIG. 2 shows that COC groups from ACC-TCGA are associated with differential somatic alteration profiles and activation of transcriptional programs. A. COC3 tumors bear a higher frequency of driver somatic alterations leading to constitutive cell cycle activation ("MUT") and higher expression of cell cycle genes measured by cell cycle score. B. COC2-3 tumors bear a higher frequency of driver somatic alterations leading to constitutive Wnt pathway activation ("MUT") and higher expression of Wnt pathway targets measured by Wnt score. C. Left—COC3 tumors frequently bear an aberrant epigenetic landscape characterized by non-physiological DNA methylation directed to CpG islands, "CIMP-high," and have higher expression of epigenetic enzymes measured by Epigenetics score; Middle—COC2+3 tumors are dominated by a "Steroid-high" and "Steroid-high/Proliferative." transcriptional program, and have higher expression of steroidogenic enzymes measured by "Steroid score"; Right—ACC-TCGA identified that ACC in bulk is largely immune poor compared to other cancers, but COC1 have a higher degree of immune infiltration measured by "Immune score."

FIG. 6. A threshold of BUB1B-PINK1 enables reasonable discrimination between COC1 and COC2-3 tumors in patients with non-CIMP-high, progressive disease.

FIG. 7. Cumulative distribution function of BUB1B-PINK1 score in ACC-TCGA enables identification of comparable BUB1B-PINK1 cutoff by qPCR in FMUSP+UM cohort.

DEFINITIONS

Figure 1:
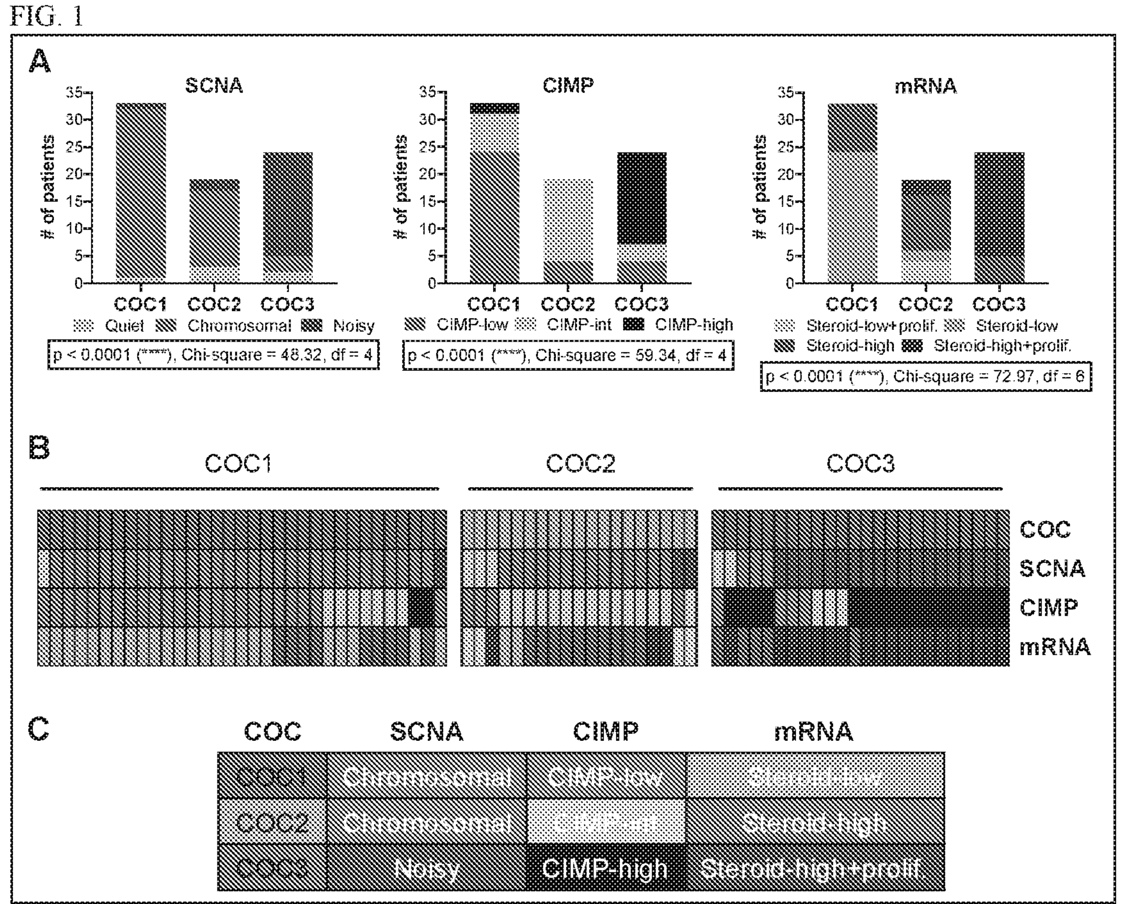
FIG. 1 shows that ACC-TCGA identifies three distinct multi-platform molecular subtypes of ACC (COC1-COC3) that can be distilled down to single platform features. A. Specific types of somatic copy number alteration profiles (SCNA), CpG island methylator phenotypes (CIMP), and mRNA subtypes converge on each COC. B. Heatmap showing SCNA, CIMP and mRNA classification for each sample bearing COC assignment in ACC-TCGA. C. Dominant SCNA, CIMP, and mRNA group for each COC.

To facilitate an understanding of the present disclosure, a number of terms and phrases are defined below:

As used herein, the term "sensitivity" is defined as a statistical measure of performance of an assay (e.g., method, test), calculated by dividing the number of true positives by the sum of the true positives and the false negatives.

As used herein, the term "specificity" is defined as a statistical measure of performance of an assay (e.g., method, test), calculated by dividing the number of true negatives by the sum of true negatives and false positives.

As used herein, the term "informative" or "informativeness" refers to a quality of a marker or panel of markers, and specifically to the likelihood of finding a marker (or panel of markers) in a positive sample.

As used herein, the term "metastasis" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body. As used herein, the term "metastasized ACC cancer cells" is meant to refer to ACC cancer cells which have metastasized.

The term "neoplasm" as used herein refers to any new and abnormal growth of tissue. Thus, a neoplasm can be a non-malignant neoplasm, a premalignant neoplasm or a malignant neoplasm. The term "neoplasm-specific marker" refers to any biological material that can be used to indicate the presence of a neoplasm. Examples of biological materials include, without limitation, nucleic acids, polypeptides, carbohydrates, fatty acids, cellular components (e.g., cell membranes and mitochondria), and whole cells.

As used herein, the term "amplicon" refers to a nucleic acid generated using primer pairs. The amplicon is typically single-stranded DNA (e.g., the result of asymmetric amplification), however, it may be RNA or dsDNA.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611: herein incorporated by reference in its entirety), assembly PCR (see, e.g., U.S. Pat. No. 5,965,408: herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specific PCR, inverse PCR (see, e.g., Triglia, et al. (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al., (1992) Biotechnology 10:413417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478485; each of which are herein incorporated by reference in their entireties). Polynucleotide amplification also can be accomplished using digital PCR (see, e.g., Kalinina, et al., Nucleic Acids Research. 25;

1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

As used herein, the terms “complementary” or “complementarity” are used in reference to polynucleotides (i.e., a sequence of nucleotides) related by the base-pairing rules. For example, the sequence “5'-A-G-T-3',” is complementary to the sequence “3'-T-C-A-5'.” Complementarity may be “partial,” in which only some of the nucleic acids' bases are matched according to the base pairing rules. Or, there may be “complete” or “total” complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term “primer” refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like) and at a suitable temperature and pH). The primer is typically single stranded for maximum efficiency in amplification but may alternatively be double stranded. If double stranded, the primer is generally first treated to separate its strands before being used to prepare extension products. In some embodiments, the primer is an oligodeoxyribonucleotide. The primer is sufficiently long to prime the synthesis of extension products in the presence of the inducing agent. The exact lengths of the primers will depend on many factors, including temperature, source of primer and the use of the method. In certain embodiments, the primer is a capture primer.

As used herein, the term “nucleic acid molecule” refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxy-amino-methyl-2-thiouracil, beta-D-mannosylqueosine, 5'-methoxycarbonylmcthyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term “nucleobase” is synonymous with other terms in use in the art including “nucleotide,” “deoxynucleotide,” “nucleotide residue,” “deoxynucleotide residue,” “nucleotide triphosphate (NTP),” or deoxynucleotide triphosphate (dNTP).

An “oligonucleotide” refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. To further illustrate, oligonucleotides are typically less than 200 residues long (e.g., between 15 and 100), however, as used herein, the term is also intended to encompass longer polynucleotide chains. Oligonucleotides are often referred to by their length. For example, a 24 residue oligonucleotide is referred to as a “24-mer”. Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Further, oligonucleotides are typically single-stranded. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) Meth Enzymol. 68: 90-99; the phosphodiester method of Brown et al. (1979) Meth Enzymol. 68: 109-151; the diethylphosphoramidite method of Beaucage et al. (1981) Tetrahedron Lett. 22: 1859-1862; the triester method of Matteucci et al. (1981) J Am Chem Soc. 103:3185-3191; automated synthesis methods; or the solid support method of U.S. Pat. No. 4,458,066, entitled “PROCESS FOR PREPARING POLYNUCLEOTIDES,” issued Jul. 3, 1984 to Caruthers et al., or other methods known to those skilled in the art. All of these references are incorporated by reference.

A “sequence” of a biopolymer refers to the order and identity of monomer units (e.g., nucleotides, etc.) in the biopolymer. The sequence (e.g., base sequence) of a nucleic acid is typically read in the 5' to 3' direction.

As used herein, “methylation” refers to cytosine methylation at positions C5 or N4 of cytosine, the N6 position of adenine, or other types of nucleic acid methylation. In vitro amplified DNA is unmethylated because in vitro DNA amplification methods do not retain the methylation pattern of the amplification template. However, “unmethylated DNA” or “methylated DNA” can also refer to amplified DNA whose original template was unmethylated or methylated, respectively.

“Methylation status” refers to the presence, absence, and/or quantity of methylation at a particular nucleotide or nucleotides within a portion of DNA. The methylation status of a particular DNA sequence (e.g., a gene marker or DNA region as described herein) can indicate the methylation state of every base in the sequence or can indicate the methylation state of a subset of the base pairs (e.g., of one or more cytosines) within the sequence, or can indicate information regarding regional methylation density within the sequence without providing precise information of where in the sequence the methylation occurs. The methylation status can optionally be represented or indicated by a “methylation value.” A methylation value can be generated, for example, by quantifying the amount of intact DNA present following restriction digestion with a methylation dependent restriction enzyme or by comparing amplification profiles after bisulfite reaction or by comparing sequences of bisulfite-treated and untreated DNA. Accordingly, a value, e.g., a methylation value, represents the methylation status and can thus be used as a quantitative indicator of methylation status across multiple copies of a locus. This is of particular use when it is desirable to compare the methylation status of a sequence in a sample to a threshold or reference value.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

The term "gene" refers to a nucleic acid (e.g., DNA) sequence that comprises coding sequences necessary for the production of a polypeptide, RNA (e.g., including but not limited to, mRNA, tRNA and rRNA) or precursor. The polypeptide, RNA, or precursor can be encoded by a full-length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences". Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) processed transcript. The mRNA functions during translation to specify the sequence or order of amino acids in a nascent polypeptide.

The term "locus" as used herein refers to a nucleic acid sequence on a chromosome or on a linkage map and includes the coding sequence as well as 5' and 3' sequences involved in regulation of the gene.

DETAILED DESCRIPTION OF THE DISCLOSURE

The present disclosure relates to compositions, systems, and methods for treating cancer. In particular, the present disclosure relates to compositions, systems, and methods for utilizing gene expression and methylation profiles to stratify and treat adrenocortical carcinoma and drugs which have utility for patients stratified by these means.

Recent comprehensive genomics studies such as The Cancer Genome Atlas study on ACC (ACC-TCGA) indicated that ACC may be better stratified using molecular stratification rather than proliferation measurements (KI67 or mitotic counts). ACC-TCGA demonstrated that ACC is a molecularly heterogeneous disease, comprised largely of 3 distinct molecular subtypes—COC1, COC2, and COC3 (Zheng et al., Cancer Cell 2016). Notably, these molecular subtypes are characterized by a distinct pattern of somatic alterations, activation of unique transcriptional programs, and profound changes in epigenetic patterning. Importantly, COC1-3 status predicts disease course under standard of care therapies—patients with COC1 disease largely have favorable prognosis, those with COC2 disease have intermediate prognosis, and those with COC3 disease have uniformly dismal prognosis.

While stratification of ACC based on molecular subtyping therefore seems promising, strategies to incorporate molecular classes into clinically feasible tests have remained elusive. An ideal molecular biomarker would be rapidly measurable by a simple assay and would reliably capture a well-defined molecular class. ACC-TCGA revealed that COC3 ACC is characterized by a pattern of genome-wide DNA methylation targeting CpG islands known as "CIMP-high;" this data indicates that DNA methylation-based molecular biomarkers enable the reliable identification of CIMP-high/COC3 tumors. In fact, it was recently demonstrated that accurately distinguishing CIMP-high from non-CIMP-high ACC can be accomplished using a simple, overnight restriction digestion/qPCR-based molecular assay to quantify CpG island methylation in the G0S2 locus (Mohan, Lerario et al., Clinical Cancer Research 2019). Furthermore, it was demonstrated that including a second qPCR-based assay to measure the mRNA expression of BUB1B and PINK1 and to calculate a score resulting from subtraction of the Ct values of BUB1B-PINK1 further stratifies ACC into "high-risk", "intermediate-risk", and "low-risk" prognostic groups based on likelihood of disease progression after surgery and development of metastatic disease at any time. Accordingly, while "high-risk" patients almost invariably recur after complete surgical resection and exhibit rapid progression of metastatic disease, "low-risk" patients never recur or present with metastatic disease. These categories thus provide a molecular risk stratification approach based on these molecular biomarkers for clinical management of ACC patients.

The above described molecular stratification strategy for prognosticating ACC is described in co-pending Pat. Ap. No. WO 2019/108568: herein incorporated by reference in its entirety). However, such classification methods do not provide customized therapies based on molecular classifications. Accordingly, provided herein are methods of using COC1-3 classification to determine a treatment course of action, screen candidate therapeutics for efficacy, and treat ACC based on ACC classification according to its associated molecular markers.

One such class of drugs are agents that block IGF1R signaling. As used herein, the term "agents that block IGF1R signaling" refers to any agent that blocks signaling by or through IGF1R. Examples include but are not limited to, inhibitors or enhancers of upstream or downstream signaling partners, modulators, or ligands of IGF1R. For example, in some embodiments, such agents decrease ligand (e.g., IGF2, IGF1) level, availability or access to the IGF1R receptor; bind (e.g., extracellular or intracellular) and antagonize the IGF1R (e.g., antibody or small molecule kinase inhibitor) and/or downstream IGF1R signaling pathway.

In some embodiments, the agent is an IGF1R inhibitor. Linsitinib is an IGF1R inhibitor, which was studied in patients with ACC but failed to reach the primary endpoint of the GALACCTIC Phase 3 clinical study, resulting in discontinuation of its development. However, a small group of patients had meaningful and durable responses indicative of drug activity, while drug toxicities were limited and manageable. Unfortunately, prior to the present disclosure, there has been no method by which to identify patients in this subpopulation of responders to IGF1R inhibitors such as linsitinib, and, thus, for whom treatment with an IGF1R inhibitor such as linsitinib are unexpectedly effective.

In particular, the original Phase 3 study evaluating efficacy of linsitinib (also known as OSI-906) in patients with advanced adrenocortical carcinoma (ACC) is published in Fassnacht et al. *Lancet Oncology* 2015. Fassnacht et al. reported no statistical difference between the Kaplan-Meier progression-free survival curves of linsitinib-treated and placebo-treated patients. However, re-examining this data, it was observed that a small subset of patients treated with linsitinib and no patients treated with placebo exhibited long-term durable response (progression-free survival >150 days).

During development of embodiments of the present disclosure, a detailed analysis of the data from this clinical trial, including molecular analysis (described in detail in Example 2) unexpectedly identified a unique patient population expected to respond to treatment with an agent that blocks IGF1R signaling (e.g. an IGF1R inhibitor such as linsitinib), while excluding patients unlikely to respond to such an agent. As described in Example 2, molecular analysis identified the responders in the trial as having molecular markers indicative of COC1 ACC. This provides a specific patient population for treatment with an agent that blocks IGF1R signaling (e.g., IGF1R inhibitors such as linsitinib), and, furthermore, had this method of treatment been employed in the clinical trial, by which patients are initially tested to assess if they have COC1 ACC and only enrolled if they are, this failed clinical study would, instead, have shown linsitinib to have had clinically meaningful efficacy relative to placebo.

For example, in some embodiments, subjects with COC1 ACC are administered an agent that blocks IGF1R signaling (e.g., IGF1R inhibitors). In some embodiments, as described in more detail below, subjects with G0S2 methylation below a threshold level are administered an agent that blocks IGF1R signaling (e.g., IGF1R inhibitors). In some embodiments, in addition to G0S2 methylation, BUB1B-PINK1 scores above a threshold limit are administered an agent that blocks IGF1R signaling (e.g., IGF1R inhibitors). In addition, in some embodiments, subjects lacking the molecular markers indicative of response to an agent that blocks IGF1R signaling (e.g., IGF1R inhibitors) are offered alternative treatments.

The present disclosure thus provides compositions and methods for treating a specific subset of ACC patients with markedly improved efficacy and demonstrated safety (See e.g., Example 3) compared with the status quo, which results in improved patient care and provides new treatment options for this difficult to treat disease.

The below description describes compositions and methods for identifying patients for treatment with specific therapies and providing such therapies.

1. Identification of ACC Classification

As described herein, in some embodiments, provided are compositions and methods for classifying ACC based on the expression or level of one or more ACC markers (e.g., BUB1B, PINK1, or G0S2) and methylation status of G0S2. In some embodiments, an expression and/or methylation score is used to characterize ACC. In some embodiments, the characterizing comprises determining a BUB1B-PINK1 expression score.

Exemplary detection and scoring methods are described below.

A. Detection Assays

In some embodiments, RNA is detection by Northern blot analysis. Northern blot analysis involves the separation of RNA and hybridization of a complementary labeled probe. In some embodiments, RNA (or corresponding cDNA) is detected by hybridization to an oligonucleotide probe). A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In some embodiments, microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays arc utilized for measuring cancer marker mRNA levels. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limited to: printing with fine-pointed pins onto glass slides: photolithography using pre-made masks: photolithography using dynamic micromirror devices; ink-jet printing; or, electrochemistry on microelectrode arrays.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. No. 5,639,606, 5,643,765, and 5,876,978 (each of which is herein incorporated by reference) is utilized. In some embodiments, the cancer markers are detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174; Nelson et al., Nonisotopic Probing, Blotting, and Sequencing, ch. 17 (Larry J. Kricka ed., 2d ed. 1995, each of which is herein incorporated by reference in its entirety).

The interaction between two molecules can also be detected, e.g., using fluorescence energy transfer (FRET) (see, for example, Lakowicz et al. U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label should be maximal. A FRET binding event can be conveniently measured through fluorometric detection means.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed, for example, in U.S. Pat. Nos. 5,925,517 and 6,150,097, herein incorporated by reference in its entirety. By way of non-limiting example, probe binding pairs having interacting labels, such as those disclosed in U.S. Pat. No. 5,928,862 (herein incorporated by reference in its entirety) might be adapted for use in method of embodiments of the present disclosure. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products methods of embodiments of the present disclosure. See, e.g., U.S. Pat. No. 5,814,447 (herein incorporated by reference in its entirety).

In some embodiments, nucleic acid sequencing methods are utilized for detection. In some embodiments, the sequencing is Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in Genomics. 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

DNA sequencing techniques include fluorescence-based sequencing methodologies (See, e.g., Birren et al., Genome Analysis: Analyzing DNA, 1, Cold Spring Harbor, N.Y.; herein incorporated by reference in its entirety). In some embodiments, the sequencing is automated sequencing. In some embodiments, the sequencing is parallel sequencing of partitioned amplicons (PCT Publication No: WO2006084132 to Kevin McKernan et al., herein incorporated by reference in its entirety). In some embodiments, the sequencing is DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. No. 5,695,934: U.S. Pat. No. 5,714,330; herein incorporated by reference in their entireties), and the Adessi PCR colony technology (Adessi et al. (2000). Nucleic Acid Res. 28, E87; WO 00018957; herein incorporated by reference in its entirety).

A variety of nucleic acid sequencing methods are contemplated for use in the methods of the present disclosure including, for example, chain terminator (Sanger) sequencing, dye terminator sequencing, and high-throughput sequencing methods. See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299:682-686 (2003): Korlach et al., Proc. Natl. Acad. Sci. USA 105:1176-1181 (2008); Branton et al., Nat. Biotechnol. 26(10):1146-53 (2008); Eid et al., Science 323:133-138 (2009); each of which is herein incorporated by reference in its entirety.

Next-generation sequencing (NGS) methods share the common feature of massively parallel, high-throughput strategies, with the goal of lower costs in comparison to older sequencing methods (see, e.g., Levy and Meyers. Annual Review of Genomics and Human Genetics Volume 17, 2016 pp 95-115; herein incorporated by reference in its entirety) A number of commercial platforms for NGS are available (See e.g., Levy and Meyers, supra).

In mammals, methylation occurs only at cytosine residues and more specifically only on a cytosine residue that is adjacent to a guanine residue (that is, at the sequence CG, often denoted "CpG"). Detecting and mapping sites of DNA methylation are essential steps for understanding epigenetic gene regulation and providing diagnostic tools for identifying cancers and other disease states associated with errors in gene regulation.

Mapping the state of DNA methylation at particular sites is currently accomplished by the bisulfite method described by Frommer, et al. for the detection of 5-methylcytosines in DNA (*Proc. Natl. Acad. Sci. USA* 89: 1827-31 (1992), explicitly incorporated herein by reference in its entirety for all purposes) or variations thereof. The bisulfite method of mapping 5-methylcytosines is based on the observation that cytosine, but not 5-methylcytosine, reacts with hydrogen sulfite ion (also known as bisulfite). The reaction is usually performed according to the following steps: first, cytosine reacts with hydrogen sulfite to form a sulfonated cytosine. Next, spontaneous deamination of the sulfonated reaction intermediate results in a sulfonated uracil. Finally, the sulfonated uracil is desulfonated under alkaline conditions to form uracil. Detection is possible because uracil forms base pairs with adenine (thus behaving like thymine), whereas 5-methylcytosine base pairs with guanine (thus behaving like cytosine). This makes the discrimination of methylated cytosines from non-methylated cytosines possible by, e.g., bisulfite genomic sequencing (Grigg G, & Clark S, Bioessays (1994) 16: 431-36; Grigg G. DNA Seq. (1996) 6: 189-98) or methylation-specific PCR (MSP) as is disclosed, e.g., in U.S. Pat. No. 5,786,146.

A gene's methylation state is often expressed as the fraction or percentage of individual strands of DNA that are methylated at a particular site (e.g., at a single nucleotide or at a longer sequence of interest, e.g., up to a ~100-bp subsequence of a DNA) relative to the total population of DNA in the sample comprising that particular site. Traditionally, the amount of unmethylated (e.g., native) gene is determined by PCR using calibrators. Then, a known amount of DNA is bisulphite treated and the resulting methylation-specific sequence is determined using either a real-time PCR or an equivalent exponential amplification.

For example, conventional methods generally comprise generating a standard curve for the unmethylated target by using external standards. The standard curve is constructed from at least two points and relates the real-time Cc value for unmethylated DNA to known quantitative standards. Then, a second standard curve for the methylated target is constructed from at least two points and external standards. This second standard curve relates the $C_t$ for methylated DNA to known quantitative standards. Next, the test sample $C_t$ values are determined for the methylated and unmethylated populations and the genomic equivalents of DNA are calculated from the standard curves produced by the first two steps. The percentage of methylation at the site of interest is calculated from the amount of methylated DNAs relative to the total amount of DNAs in the population, e.g., (number of methylated DNAs)/(the number of methylated DNAs+number of unmethylated DNAs)×100.

The present disclosure is not restricted in the method by which a gene's methylation state is measured. For example, in some embodiments the methylation state is measured by a genome scanning methods. For example, one method involves restriction landmark genomic scanning (Kawai et al., Mol. Cell. Biol. 14:7421-7427, 1994) and another example involves methylation-sensitive arbitrarily primed PCR (Gonzalgo et al., Cancer Res. 57:594-599, 1997). In some embodiments, changes in methylation patterns at specific CpG sites are monitored by digestion of genomic DNA with methylation-sensitive restriction enzymes followed by Southern analysis of the regions of interest (digestion-Southern method). In some embodiments, analyzing changes in methylation patterns involves a PCR-based process that involves digestion of genomic DNA with methylation-sensitive restriction enzymes prior to PCR (e.g., qPCR) amplification (Singer-Sam et al., Nucl. Acids Res. 18:687, 1990 or commercially available from Qiagen. Hilden, Del.)). In addition, other techniques have been reported that utilize bisulfite treatment of DNA as a starting point for methylation analysis. These include methylation-specific PCR (MSP) (Herman et al. Proc. Natl. Acad. Sci. USA 93:9821-9826, 1992) and restriction enzyme digestion of PCR products amplified from bisulfite-converted DNA (Sadri and Hornsby, Nucl. Acids Res. 24:5058-5059, 1996; and Xiong and Laird, Nucl. Acids Res. 25:2532-2534, 1997). PCR techniques have been developed for detection of gene mutations (Kuppuswamy et al., Proc. Natl. Acad. Sci. 55 USA 88:1143-1147, 1991) and quantification of allelic-specific expression (Szabo and Mann, Genes Dev. 9:3097-3108, 1995; and Singer-Sam et al., PCR Methods Appl. 1:160-163, 1992). Such techniques use internal primers, which anneal to a PCR-generated template and terminate immediately 5' of the single nucleotide to be assayed. Methods using a "quantitative Ms-SNuPE assay" as described in U.S. Pat. No. 7,037,650 are used in some embodiments.

Compositions for use in the methods described herein include, but are not limited to, kits comprising one or more reagents for determining the level of expression of BUB1B, PINK1, and G0S2 and the methylation status of G0S2 as described above. In some embodiments, the reagents are, for example, a nucleic acid probe or probes that hybridizes to BUB1B, PINK1, and G0S2, one or more nucleic acid primers for the amplification or extension of BUB1B, PINK1, and G0S2, one or more methylation specific restriction enzymes, or one or more nucleic acid primers that bind specifically to methylated G0S2 nucleic acids.

The probes may also be provided in the form of an array. In preferred embodiments, the kits contain all the components necessary to perform a detection assay, including all controls, directions for performing assays, and any necessary software for analysis and presentation of results.

B. COC classification

As described herein, the expression levels of BUB1B and PINK1 and the methylation levels of G0S2 are used to classify COC into subtypes COC1-3.

The present disclosure is not limited to particular cut-off or threshold values for characterizing ACC. For example, in some embodiments, a BUB1B-PINK1 expression score above a threshold level, and a G0S2 methylation of less than a threshold level (e.g., less than 4.696%, 4.6%, or 4.5%) is indicative of COC1. In some embodiments, the cut-off value for G0S2 methylation levels is less than 4.696% plus or minus 1%, 5%, or 10%.

In some embodiments, a BUB1B-PINK1 expression score below a threshold level, and a G0S2 methylation of below a threshold level (e.g., less than 4.696%, 4.6%, or 4.5%) is indicative of COC2. In some embodiments, the cut-off value for G0S2 methylation levels is less than 4.696% plus or minus 1%, 5%, or 10%.

In some embodiments, the presence of G0S2 methylation of greater than a threshold level (e.g., greater than 4.696%, 4.6%, 4.7%, 4.8%, 4.9%, or 5.0%) is indicative of COC3. In some embodiments, the cut-off value for G0S2 methylation levels is less than 4.696% plus or minus 1%. 5%, or 10%.

The present disclosure is not limited to particular threshold levels for BUB1B PINK1 expression scores (e.g., to differentiate between COC1 and COC2). In some embodiments, the BUB/B-PINK1 expression score threshold level is 1.4 to 1.8 (e.g., 1.4, 1.5, 1.6, 1.7, or 1.8). In some embodiments, BUB1B-PINK1 expression score threshold is 1.646 plus or minus 1%, 5%, or 10%.

In some embodiments, the BUB1B-PINK1 expression score is based on the subtraction of the delta Ct values of BUB1B and PINK1.

In some embodiments, the BUB1B-PINK1 expression score is determined by subtraction of z-scores of gene expression when BUB1B and PINK1 are measured using alternative techniques including RNA-seq.

In some embodiments, BUB1B-PINK1 expression score and G0S2 methylation values displayed in Table 1 (e.g., plus or minus plus or minus 1%, 5%, or 10%) are utilized to characterizing ACC.

In the case where higher resolution approaches are being applied to evaluate G0S2 methylation, the numerical cutoff for classifying a sample as possessing G0S2 methylation may vary. This is because higher resolution approaches to evaluate G0S2 methylation take measurement of numerous CpG resides residing in and around the G0S2 locus rather than reducing methylation to a single value. Notably, the distribution of average methylation across the G0S2 locus in a population of patients with ACC is bimodal and does not vary with the measurement strategy adopted as demonstrated in Mohan & Lerario et al. Clinical Cancer Research 2019; herein incorporated by reference in its entirety. In the event the user is taking a higher resolution approach to measure G0S2 methylation including but not limited to genome-wide DNA methylation arrays or next-generation sequencing-based approaches including targeted bisulfite sequencing, an alternative method is used to classify samples as having a G0S2 methylation level above or below a threshold level. For example, in some embodiments, unsupervised complete hierarchical clustering using Euclidean distance on logit-transformed methylation beta-values (or equivalent values) of CpG residues residing in and around the G0S2 locus are used to classify samples as above or below a methylation threshold as described in Mohan & Lerario et al. Clinical Cancer Research 2019 (e.g., samples in the lower methylation distribution are classified as below the threshold and sample in the upper methylation distribution are classified as above the threshold level).

Also, as described herein, in some embodiments, in the case where higher resolution approaches are being applied to evaluate BUB1B-PINK1 score, including but not-limited to, a targeted RNA-seq panel, the BUB1B-PINK1 expression score is computed using subtraction of z-scores of expression and is calibrated according to percentile of expression. Note that when the BUB1B-PINK1 expression score is computed using difference of z-scores, the directionality of the score is inverted; samples with G0S2 methylation below a threshold level and BUB1B-PINK1 score above a threshold level are in this instance classified as COC2, and samples with G0S2 methylation below a threshold level and BUB1B-PINK1 score below a threshold level are classified as COC1. For example, in some embodiments, the threshold level for BUB1B-PINK1 score to stratify patients is the 44th percentile of non-CIMP-high patients with a history of metastatic disease.

In some embodiments, ACC classification (e.g., COC1-3) is used to recommend a treatment or candidate treatment to a subject with ACC and/or administer the treatment.

In some embodiments, a computer-based analysis program is used to translate the raw data generated by the detection assay (e.g., the expression level or methylation level of a given marker or markers) into data of predictive value for a clinician. The clinician can access the predictive data using any suitable means. Thus, in some preferred embodiments, the present disclosure provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present disclosure contemplates any method capable of receiving, processing, and transmitting the information to and from laboratories conducting the assays, information provides, medical personal, and subjects. For example, in some embodiments of the present disclosure, a sample (e.g., a biopsy or a blood or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression or methylation data), specific for the diagnostic or prognostic information desired for the subject.

The profile data is then prepared in a format suitable for interpretation by a treating clinician. For example, rather than providing raw expression data, the prepared format may represent a diagnosis or risk assessment for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject can directly access the data using the electronic communication system. The subject may choose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action. In some embodiments, the results are used to select candidate therapies for drug screening or clinical trials.

II. Treatment of ACC

In some embodiments, molecular classification of ACC is used to recommend and administer a treatment for ACC. COC1-3 molecular subtypes are characterized by enrichment for distinct transcriptional programs that arc targeted by these pharmacological agents, individually or in combination therapies. Therefore, classification of ACC into COC1-3 enables the pre-selection of a patient population most likely to respond to a given targeted agent (or combination of targeted agents) and offers a method of treatment with such agent(s) to increase the effectiveness of such agent(s) by focusing use in patients most likely to benefit. As well, such focused use will reduce or eliminate use in patients not likely to benefit, thereby reducing or avoiding unnecessary drug toxicity as well as saving money spent and avoiding patient dissatisfaction when agents are ineffective.

For example, FIG. 1 shows that ACC-TCGA (Zheng et al. Cancer Cell 2016) identifies three distinct multi-platform molecular subtypes of ACC (COC1-COC3) which may be distilled down to single platform features. Specific types of somatic copy number alteration profiles (SCNA) derived from SNP array profiling, CpG island methylator phenotypes (CIMP) derived from array-based DNA methylation profiling, and mRNA subtypes derived from RNA-seq transcriptome profiling, converge on each COC as measured by the Chi-square test (A) or as a heatmap (B) FIG. 1C shows the dominant SCNA, CIMP, and mRNA group for each COC. Notably, as described herein and particularly relevant for Examples 1-2. COC3 tumors possess a CIMP-high DNA methylation profile and noisy SCNA profile. Each COC is associated with distinct prognosis—COC1 (good, slower disease kinetics), COC2 (intermediate, moderate disease kinetics), COC3 (dismal, rapidly progressive disease kinetics).

Analysis of ACC-TCGA data revealed that while 90% of ACC tumors across all 3 molecular classes (COC1, COC2, COC3) of ACC exhibit high expression of IGF2 (and therefore IGF1R-induced signaling) (Zheng et al. *Cancer Cell* 2016), COC3/CIMP-high tumors are uniquely characterized by an additional strong induction of E2F-dependent transcription (including cell cycle genes, DNA repair genes, and epigenetic writers such as EZH2 and DNMT1), high levels of NR5A1-dependent steroidogenesis, and high levels of canonical Wnt signaling activation. In addition, COC3/CIMP-high ACC bear low expression of immune cell transcriptional markers, consistent with immune cell exclusion in these tumors.

Figure 3:
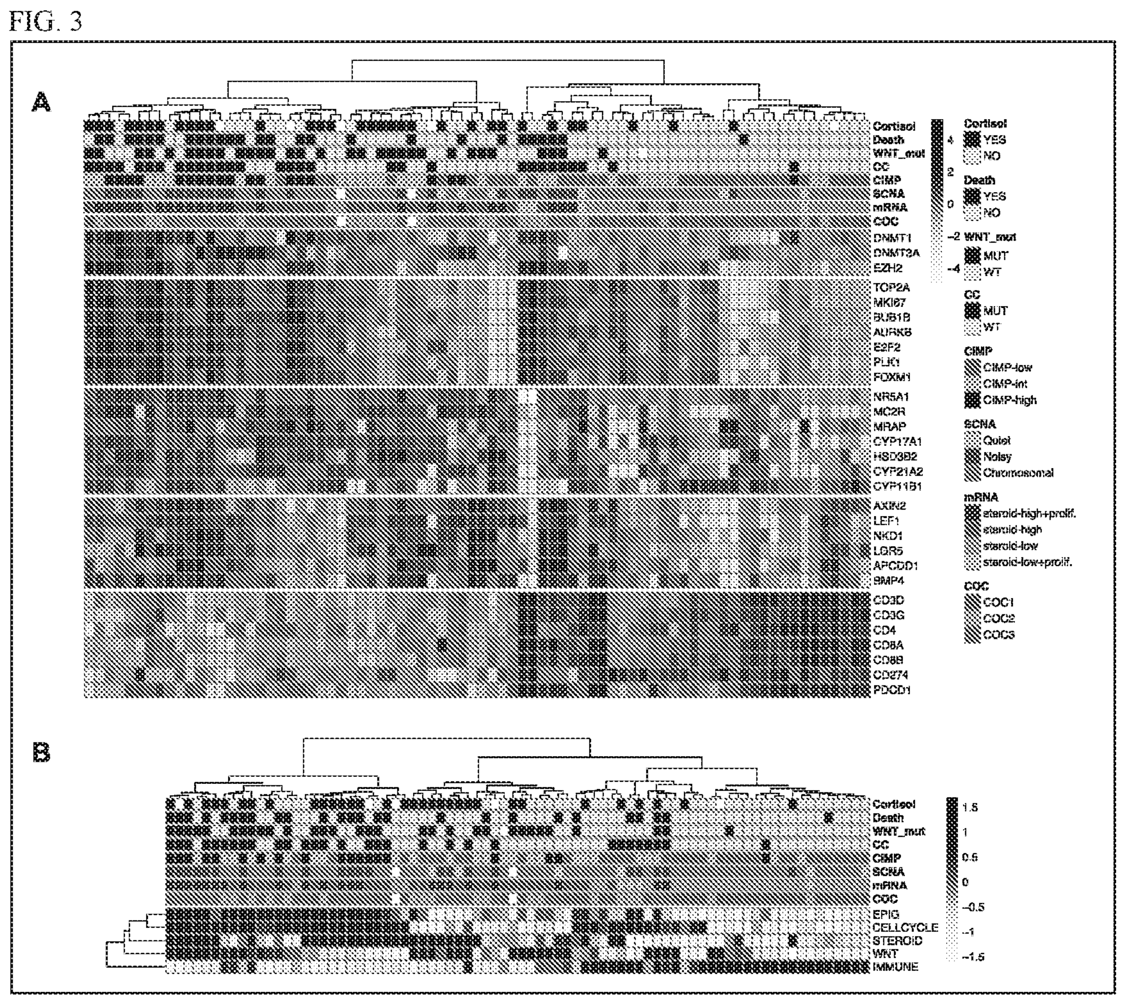
FIG. 3 shows a heatmap depicting information from FIGS. 1 and 2 on a sample by sample basis. A. Gene expression level from ACC-TCGA RNA-seq data is color-coded by row z-score (white to black). B. This heatmap depicts similar information to A, except in this case genes are collapsed into corresponding Epigenetics ("EPIG"), Cell cycle ("CELLCYCLE"), Steroid ("STEROID"), Wnt ("WNT"), and Immune ("IMMUNE") scores and scores are colored by actual value.
Figure 4:
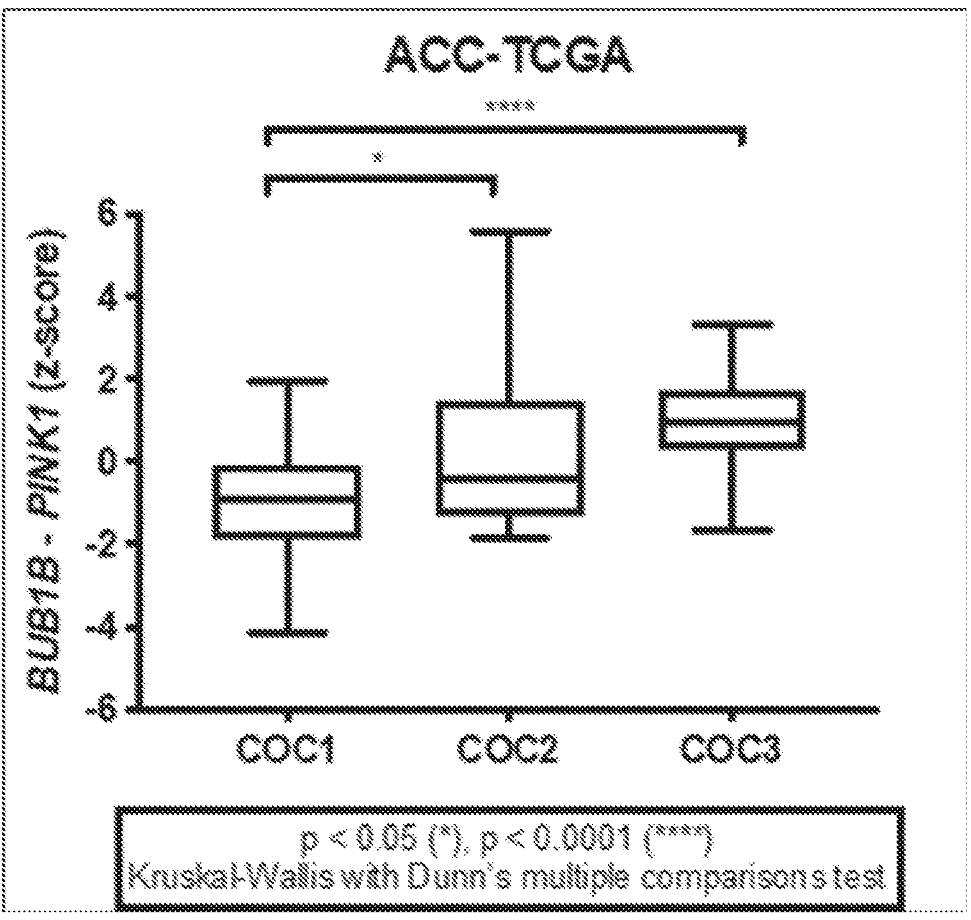
FIG. 4 shows that, in ACC-TCGA, BUB1B-PINK1 score distinguishes patients with COC1 disease from those with COC2 and COC3 tumors.
Figure 5:
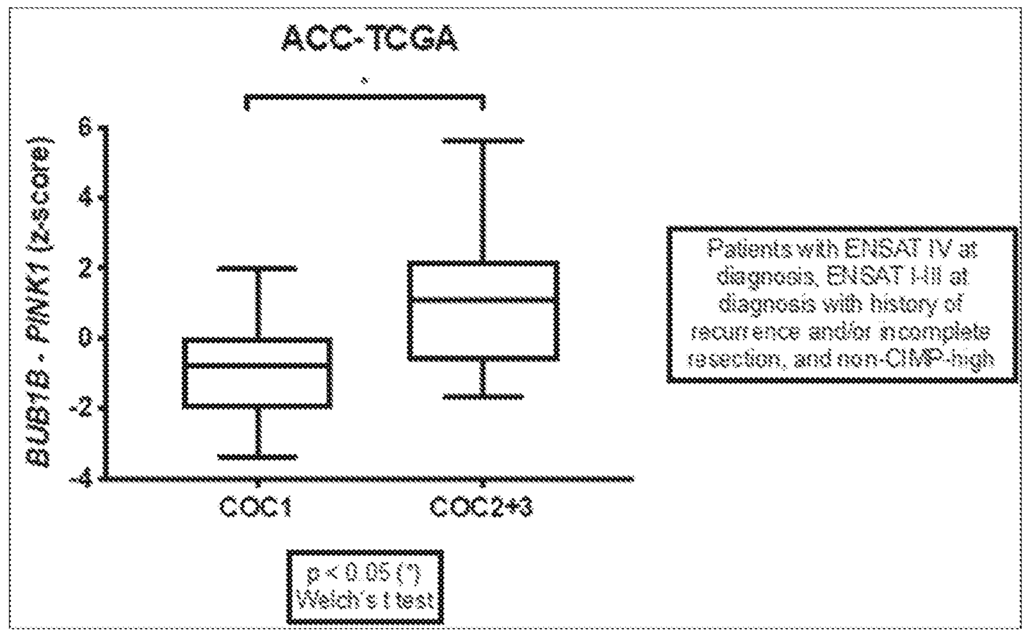
FIG. 5 shows that, in ACC-TCGA, COC1 patients with non-CIMP-high, progressive disease have statistically different BUB1B-PINK1 from COC2 patients with non-CIMP-high, progressive disease.
Figure 8:
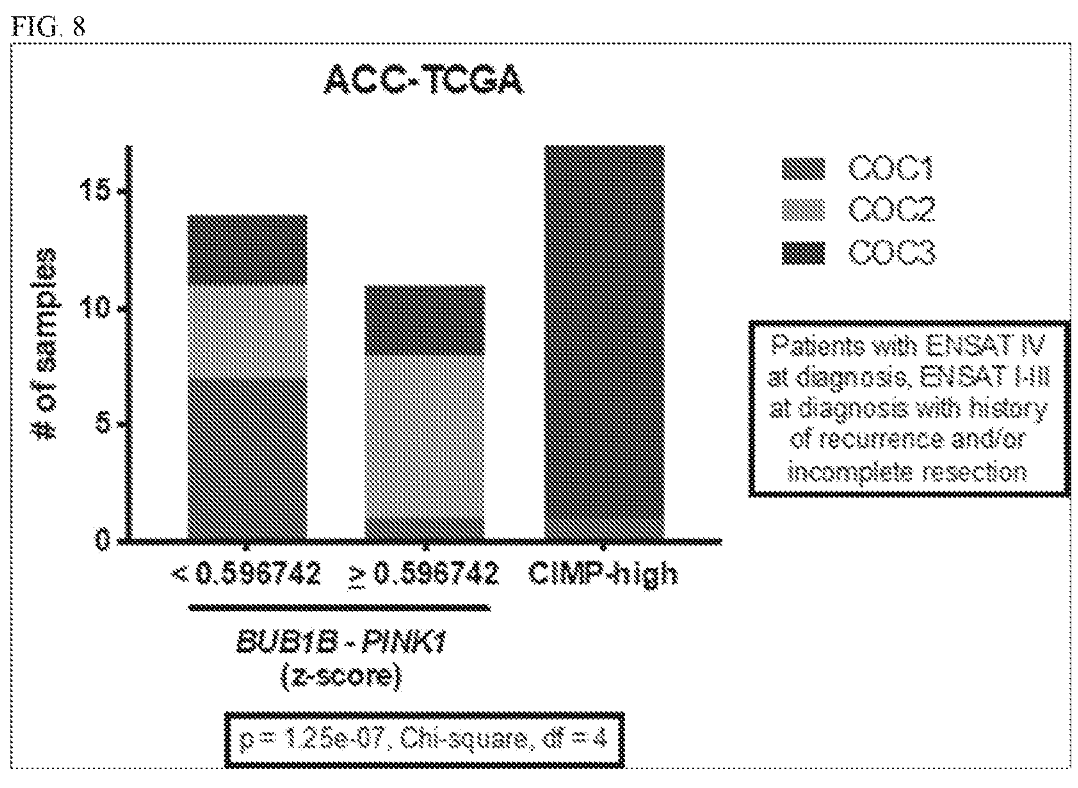
FIG. 8. BUB1B-PINK1 combined with CIMP-status faithfully recapitulates COC in patients with progressive disease.

In addition, as shown in FIGS. 2 and 3, COC groups from ACC-TCGA arc associated with differential somatic alteration profiles and activation of transcriptional programs. COC3 tumors bear a higher frequency of driver somatic alterations leading to constitutive cell cycle activation ("MUT"). Consistent with this enrichment, COC3 tumors also bear a higher cell cycle score, supporting cell cycle-targeting therapies in COC3 tumors. This cell cycle score is derived using ACC-TCGA (Zheng et al. Cancer Cell 2016) RNA-seq data and GSVA (Hanzelmann et al. BMC Bioinformatics 2013) from the expression of bona fide cell cycle and E2F target genes known to bear higher expression in cycling cells (TOP2A, MK167, BUB1B, AURKB, E2F2, PLK1, FOXM1). COC2-3 tumors bear a higher frequency of driver somatic alterations leading to constitutive Wnt pathway activation ("MUT"). Consistent with this enrichment, both COC2 and COC3 tumors bear a higher Wnt score, supporting Wnt pathway-targeting therapies in COC2+3 tumors. This Wnt score is derived using ACC-TCGA RNA-seq data and GSVA from the expression of bona fide Wnt pathway target genes (AXIN2, LEF1, NKD1, LGR5, APCDD1, BMP4).

COC3 tumors frequently bear an aberrant epigenetic landscape characterized by non-physiological DNA methylation directed to CpG islands, "CIMP-high". COC3 tumors also bear a higher epigenetics score (derived using ACC-TCGA RNA-seq and GSVA) comprised of 3 genes implicated in this program (DNMT1, DNMT3A, EZH2), supporting a role for targeted epigenetic therapies (including DNA methyltransferase inhibitors and EZH2 inhibitors) in COC3 tumors.

COC2 and COC3 tumors are dominated by a "Steroid-high" and "Steroid-high/Proliferative" transcriptional program as identified in ACC-TCGA. This program is characterized by higher expression of the adrenocortical transcription factor SF1 (encoded by NR5A1) as well as higher expression of steroidogenic enzymes. Consistent with this, an ACC-TCGA RNA-seq/GSVA-derived Steroid score comprised of genes implicated in this program (NR5A1, MC2R, MRAP, CYP17A1, HSD3B2, CYP21A2, CYP11B1) is higher in COC2 and COC3 tumors. This data supports therapies targeting SF1 and steroidogenesis in COC2 and COC3. ACC-TCGA identified that ACC in bulk is largely immune poor compared to other cancers. As shown in FIG. 2, COC1 tumors have a higher degree of immune infiltration (measured by an ACC-TCGA RNA-seq/GSVA-derived immune score, comprised of the expression of immune genes CD3D, CD3G, CD4, CD8A, CD8B, CD274, PDCD1). This supports T-cell targeting immunotherapy also referred to herein as "immune checkpoint therapy" in COC1 tumors. Finally, cortisol/glucocorticoids (the production of which is controlled by the genes used to derive the steroid score) are immunosuppressive. Thus, in some embodiments, a combination of steroidogenesis inhibition and immunotherapy is utilized to treat patients with COC2 and COC3 tumors.

FIG. 3 provides a heatmap depicting information from FIGS. 1 and 2 on a sample by sample basis, including additional information about clinical cortisol production ("Cortisol") and patient death ("Death") at the time of the study. Each sample is represented by a column, and the dendrogram depicts unsupervised hierarchical clustering performed on samples on the basis of gene expression. Wnt pathway alterations are indicated by the "WNT_mut" track and cell cycle alterations are indicated by the "CC" track. A. Gene expression level from ACC-TCGA RNA-seq data is color-coded by row z-score (white to black). Patients with COC3 tumors have more aggressive disease ("Death") and higher tumor expression of epigenetics (DNMT1, DNMT3A, EZH2) and cell cycle genes (TOP2A, MK167, BUB1B, AURKB, E2F2, PLK1, FOXM1). Patients with COC2 and COC3 disease have clinical cortisol production, more aggressive disease, and higher tumor expression of steroid (NR5A1, MC2R, MRAP, CYP17A1, HSD3B2, CYP21A2, CYP11B1) and Wnt pathway (AXIN2, LEF1, NKD1, LGR5, APCDD1, BMP4) genes. Patients with COC1 tumors have less aggressive disease, infrequently produce cortisol, and have higher expression of genes linked to immune infiltration and activation of targetable immune checkpoints (CD3D, CD3G, CD4, CD8A, CD8B, CD274, PDCD1).

FIG. 3B shows a heatmap where genes are collapsed into corresponding Epigenetics ("EPIG"), Cell cycle ("CELL-CYCLE"), Steroid ("STEROID"), Wnt ("WNT"), and Immune ("IMMUNE") scores. Scale represents actual score value (white to black). Unsupervised hierarchical clustering was performed on samples and scores on the basis of score value, demonstrating coordinate regulation of Epigenetics, Cell cycle, Steroid, and Wnt scores, and anti-correlation of these with Immune scores.

COC1 tumors are characterized by low level of E2F, low level of Wnt-dependent transcriptional programs and infrequent somatic alterations that when present lead to constitutive cell cycle and Wnt pathway activation as observed in COC3 (constitutive cell cycle and Wnt pathway activation) and COC2 (constitutive Wnt pathway activation) (FIG. 2, FIG. 3), indicating that in this molecular class IGF1R-dependent signaling is a dominant oncogenic hit. Furthermore, COC1 tumors are uniquely characterized by increased expression of immune-related genes. Therefore, pharmacological agents targeting COC1 tumors include an agent that blocks IGF1R signaling (e.g., IGF1R inhibitors) and/or immune checkpoint inhibitors.

Accordingly, in some particular embodiments, the present disclosure provides compositions and methods for treating COC1 (e.g., tumors with a level of G0S2 methylation below a threshold level and a BUB1B-PINK1 score above a threshold level) with an agent that blocks IGF1R signaling (e.g., IGF1R inhibitors (e.g., including but not limited to, linsitinib, cixutumumab, ganitumab, figitumumab, dalotuzumab, istiratumab, dusigitumab, or teprotumumab), etc. In some specific embodiments, subjects with G0S2 methylation below a threshold level and a BUB1B-PINK1 expression score above a threshold level are treated with linsitinib and subjects with a level of G0S2 methylation above a threshold level and a BUB1B-PINK1 score below a threshold level are not treated with linsitinib or other IGF1R inhibitors or agents that blocks IGF1R signaling.

In some embodiments, in addition to or instead of an agent that blocks IGF1R signaling, COC1 tumors are treated with an immune checkpoint inhibitor (e.g., an agent that targets CTLA-4, PD-1, or PD-L1).

In some embodiments, molecular targets in COC3/CIMP-high include, but are not limited to, cell cycle effectors (e.g., one or more of CDK4/6, PLK1, MELK or AURKB), DNA repair proteins (e.g., WEE1 and/or PARP), an agent that alters Wnt signaling (e.g. one or more of β-catenin, CBP, TCF, LEF, Wnt ligands, the APC/GSK3β destruction complex, and/or Porcupine), epigenetic writers (e.g., EZH2 and/or DNMT1), and NR5A1.

On the other hand, COC3/CIMP-high tumors are less likely to respond to immune checkpoint inhibitors and an agent that blocks IGF1R signaling (e.g., IGF1R inhibitors) as monotherapy. However, in some embodiments, in addition to one or more of the targets listed above, COC3 tumors are further treated with an agent that blocks IGF1R signaling and/or immune checkpoint therapy in combination with an NR5A1 inhibitor or a glucocorticoid synthesis/metabolism inhibitor or glucocorticoid receptor inhibitor.

Similarly, COC2 tumors are characterized by high canonical Wnt signaling activation, and high levels of NR5A1-dependent transcription. Therapeutic agents that target COC2 tumors include, but arc not limited to, Wnt inhibitors and/or NR5A1 antagonists. In some embodiments, in addition to one or more of the targets listed above, COC2 tumors are further treated with an agent that blocks IGF1R signaling and/or immune checkpoint therapy in combination with an NR5A1 inhibitor or a glucocorticoid synthesis/metabolism inhibitor or glucocorticoid receptor inhibitor.

The present disclosure is not limited to particular target genes or therapies. In some embodiments, the inhibitor is an antibody, a nucleic acid, or a small molecule. For example, in some embodiments, the cell cycle effector protein is CDK4/6, PLK1, MELK, or AURK and the inhibitor is palbociclib (Pfizer. New York, N.Y.). In some embodiments, the DNA repair protein is WEE1 or PARP and the inhibitor is adavosertib (Merck) or olaparib (Merck, Kenilworth, N.J.). In some embodiments, the IGF1R inhibitor is linsitinib (Achemtek, Worcester, Mass.), cixutumumab (McKian et al., Expert Opin Investig Drugs. 2009 July; 18(7): 1025-1033), figitumumab (Pfizer), ganitumab (Amgen, Thousand Oaks, Calif.), teprotumumab (Horizon Pharma), dalotuzumab (Merck/Pierre Fabre), istiratumab (Merrimack Pharma), or dusigitumab (Medimmune/AstraZeneca). In some embodiments, the Wnt inhibitor is WNT974 (Novartis, Basel, Switzerland) or PRI-724 (Prism Pharma). In some embodiments, the immune checkpoint inhibitor is ipilimumab (Bristol-Myers Squibb, New York, N.Y.), nivolumab (Bristol-Myers Squibb), pembrolizumab (Merck), or atezolizumab (Hoffmann-La Roche, Basel, Switzerland). In some embodiments, the NR5A1 inhibitor is SID 7969543 (Bio-Techne Corporation, Minneapolis, Minn.), 45594 [4-(heptyloxy)phenol] or octyloxyphenyl (OOP) (both available from ACADIA Pharmaceuticals, San Diego, Calif.). In some embodiments, the epigenetic writer is EZH2 and/or DNMT1 and the inhibitor is 3-deazaneplanocin A (Cayman, Ann Arbor, Mich.), EPZ005687 (Epizyme, Cambridge, Mass.), EPZ6438/tazemetostat (Epizyme), or 5-Azacytidine (Tocris, Minneapolis, Minn.). In some embodiments, the immune checkpoint inhibitor is Ipilimumab (Bristol-Myers Squibb, New York, N.Y.), Nivolumab (Bristol-Myers Squibb, New York, N.Y.), Pembrolizumab (Merck, Kenilworth, N.J.), Atezolizumab (Roche, Basel, Switzerland), Avelumab (Merck, Kenilworth, N.J.), Durvalumab (AstraZeneca, Cambridge, United Kingdom) and Cemiplimab (Regeneron, Tarrytown, N.Y.). In some embodiments, the glucocorticoid synthesis/metabolism inhibitor or glucocorticoid receptor inhibitor is aminoglutethimide, osilodrostat (Novartis, Basel, Switzerland), metyrapone (Catalent Germany Eberbach GmbH, Eberbach, Germany), mifepristone (Danco Laboratories, New York, N.Y.) or ketoconazole.

In some embodiments, one or more (e.g., 1, 2, 3, 4, or more) inhibitors that target the same gene or COC subtype are administered to a subject. In some embodiments, a combination of therapies directed to a particular COC subtype arc used in combination. For example, in one non-limiting example, a subject having a COC3 carcinoma is administered one or more therapies described above as targeting COC3 in combination with a Wnt inhibitor or a NR5A1 inhibitor; and an agent that blocks IGF1R signaling (e.g., IGF1R inhibitor) and/or an immune checkpoint inhibitor. In another example, a subject having a COC2 carcinoma is administered a therapy targeting COC2 described above and an agent that blocks IGF1R signaling (e.g., IGF1R inhibitor) and/or an immune checkpoint inhibitor in combination with an NR5A1 inhibitor or a glucocorticoid synthesis/metabolism inhibitor or glucocorticoid receptor inhibitor. Additional combination therapies are described herein.

In some embodiments, the inhibitor is a nucleic acid. Exemplary nucleic acids suitable for inhibiting expression of the described markers (e.g., by preventing expression of the marker) include, but arc not limited to, antisense nucleic acids and RNAi. In some embodiments, nucleic acid therapies are complementary to and hybridize to at least a portion (e.g., at least 5, 8, 10, 11, 12, 13, 14, 15, 16, 17, 18, 19, or 20 nucleotides) of a marker described herein.

In some embodiments, compositions comprising oligomeric antisense compounds, particularly oligonucleotides are used to modulate the function of nucleic acid molecules encoding a marker described herein, ultimately modulating the amount of marker gene expressed. This is accomplished by providing antisense compounds that specifically hybridize with one or more nucleic acids encoding the marker genes. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is decreasing the amount of marker expressed.

In some embodiments, nucleic acids arc RNAi nucleic acids. "RNA interference (RNAi)" is the process of sequence-specific, post-transcriptional gene silencing initiated by a small interfering RNA (siRNA), shRNA, or microRNA (miRNA). During RNAi, the RNA induces degradation of target mRNA with consequent sequence-specific inhibition of gene expression.

In "RNA interference," or "RNAi," a "small interfering RNA" or "short interfering RNA" or "siRNA" or "short hairpin RNA" or "shRNA" molecule, or "miRNA" an RNAi (e.g., single strand, duplex, or hairpin) of nucleotides is targeted to a nucleic acid sequence of interest, for example, a marker disclosed herein.

An "RNA duplex" refers to the structure formed by the complementary pairing between two regions of an RNA molecule. The RNA using in RNAi is "targeted" to a gene in that the nucleotide sequence of the duplex portion of the RNAi is complementary to a nucleotide sequence of the targeted gene. In certain embodiments, the RNAi is are targeted to the sequence encoding a marker described herein. In some embodiments, the length of the RNAi is less than 30 base pairs. In some embodiments, the RNA can be 32, 31, 30, 29, 28, 27, 26, 25, 24, 23, 22, 21, 20, 19, 18, 17, 16, 15, 14, 13, 12, 11 or 10 base pairs in length. In some embodiments, the length of the RNAi is 19 to 32 base pairs in length. In certain embodiment, the length of the RNAi is 19 or 21 base pairs in length.

In some embodiments, RNAi comprises a hairpin structure (e.g., shRNA). In addition to the duplex portion, the hairpin structure may contain a loop portion positioned between the two sequences that form the duplex. The loop can vary in length. In some embodiments the loop is 5, 6, 7, 8, 9, 10, 11, 12, 13, 14, 15, 16, 17, 18, 19, 20, 21, 22, 23, 24, 25, 26 or 27 nucleotides in length. In certain embodiments, the loop is 18 nucleotides in length. The hairpin structure can also contain 3' and/or 5' overhang portions. In some embodiments, the overhang is a 3' and/or a 5' overhang 0, 1, 2, 3, 4 or 5 nucleotides in length.

"miRNA" or "miR" means a non-coding RNA between 18 and 25 nucleobases in length which hybridizes to and regulates the expression of a coding RNA. In certain embodiments, a miRNA is the product of cleavage of a pre-miRNA by the enzyme Dicer. Examples of miRNAs are found in the miRNA database known as miRBase.

As used herein, Dicer-substrate RNAs (DsiRNAs) are chemically synthesized asymmetric 25-mer/27-mer duplex RNAs that have increased potency in RNA interference compared to traditional RNAi. Traditional 21-mer RNAi molecules are designed to mimic Dicer products and therefore bypass interaction with the enzyme Dicer. Dicer has been recently shown to be a component of RISC and involved with entry of the RNAi into RISC. Dicer-substrate RNAi molecules are designed to be optimally processed by Dicer and show increased potency by engaging this natural processing pathway. Using this approach, sustained knockdown has been regularly achieved using sub-nanomolar concentrations. (U.S. Pat. No. 8,084,599; Kim et al., Nature Biotechnology 23:222 2005; Rose et al., Nucleic Acids Res., 33:4140 2005).

The transcriptional unit of a "shRNA" is comprised of sense and antisense sequences connected by a loop of unpaired nucleotides. shRNAs are exported from the nucleus by Exportin-5, and once in the cytoplasm, are processed by Dicer to generate functional RNAi molecules. "miRNAs" stem-loops are comprised of sense and antisense sequences connected by a loop of unpaired nucleotides typically expressed as part of larger primary transcripts (pri-miRNAs), which are excised by the Drosha-DGCR8 complex generating intermediates known as pre-miRNAs, which are subsequently exported from the nucleus by Exportin-5, and once in the cytoplasm, are processed by Dicer to generate functional miRNAs or siRNAs.

"Artificial miRNA" or an "artificial miRNA shuttle vector", as used herein interchangeably, refers to a primary miRNA transcript that has had a region of the duplex stem loop (at least about 9-20 nucleotides) which is excised via Drosha and Dicer processing replaced with the siRNA sequences for the target gene while retaining the structural elements within the stem loop necessary for effective Drosha processing. The term "artificial" arises from the fact the flanking sequences (e.g., about 35 nucleotides upstream and about 40 nucleotides downstream) arise from restriction enzyme sites within the multiple cloning site of the RNAi. As used herein the term "miRNA" encompasses both the naturally occurring miRNA sequences as well as artificially generated miRNA shuttle vectors.

The RNAi can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal or a sequence of six Ts.

The present disclosure further provides pharmaceutical compositions (e.g., comprising the compounds described above). The pharmaceutical compositions of the present disclosure may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

In some embodiments, one or more targeted therapies are administered in combination with an existing therapy for ACC. For example, in some embodiments, subjects with COC3 tumors are administered adjuvant cytotoxic chemotherapy (e.g., one or more of etoposide, doxorubicin, cisplatin or other cytotoxic agents). In some embodiments, the COC classification determination is repeated (e.g., during treatment or after surgery).

In some embodiments, agents described herein are screening for activity against ACC (e.g., in vitro drug screening assays or in a clinical study).

EXPERIMENTAL

The following examples are provided in order to demonstrate and further illustrate certain preferred embodiments and aspects of the present disclosure and are not to be construed as limiting the scope thereof.

Example 1

To prospectively classify ACC samples into COC1-3 subgroups a modified version of the described two-step prognostication strategy (Mohan. Lerario et al., Clinical Cancer Research 2019) is used. The method described herein discriminates COC1, COC2, and COC3. The data reveals that G0S2 hypermethylation is almost exclusively observed in CIMP-high/COC3 (and therefore can be used to identify this aggressive molecular subtype of ACC), non-CIMP-high (COC1-2) ACC invariably exhibits low and indistinguishable levels of G0S2 methylation. However, COC1 and COC2 exhibit distinct BUB1B-PINK1 scores. In analysis of ACC-TCGA RNA-seq data. COC1 were reliably distinguished from COC2 and COC3 by the difference of z-scores of expression of BUB1B and PINK1 in recurrent/metastatic tumors (Table 1 and FIGS. 4-8). This was used to calculate the corresponding BUB1B-PINK1 score (measured by TaqMan assays) in an independent cohort of non-CIMP-high metastatic/recurrent tumors (See e.g., Mohan, Lerario et al., Clinical Cancer Research 2019). This cutoff enables the distinction between COC1 and COC2+3 using TaqMan assays. Accordingly, COC3 ACC is defined by G0S2 methylation >4.696% and any value of BUB1B-PINK1 score, COC2 ACC is characterized by G0S2 methylation <4.696% and BUB1B-PINK1 score <1.646, and COC1 ACC is characterized by G0S2 methylation <4.696% and BUB1B-PINK1 score >1.646 (Table 1). The application of this strategy is not restricted to the availability of fresh/frozen tissue samples, being extensible to embedded frozen, or formalin-fixed paraffin-embedded (FFPE) samples from ACC samples.

TABLE 1

Cutoffs for G0S2 methylation and BUB1B-PINK1 score (measured by EpiTect and TaqMan assays, respectively, from frozen tissue) to classify ACC into ACC-TCGA COC1-3 molecular classes.

| ACC-TCGA molecular class | G0S2 methylation | BUB1B-PINK1 score |
|---|---|---|
| COC1 | <4.696% | >1.646 |
| COC2 | <4.696% | ≤1.646 |
| COC3 | >4.696% | Any value |

Example 2

ACC-TCGA (Zheng et al. *Cancer Cell* 2016) identified that there are 3 types of ACC, namely COC1, COC2 and COC3. These types are characterized by unique molecular features, i.e. specific copy number alteration profiles (SCNA). DNA methylation profiles (CIMP), and mRNA profiles (mRNA) as depicted in FIG. 1.

COC1, COC2, and COC3 progress at different rates. Among all patients enrolled in ACC-TCGA, patients with COC1 disease had slowly progressive disease (did not reach median event-free survival), patients with COC2 disease had moderately progressive disease (median event-free survival of 38 months), and patients with COC3 disease had rapidly progressive disease (median event-free survival of 8 months). However, even though COC1, COC2, and COC3 progress at different rates, all types of ACC may evolve to metastatic disease, and the majority of all patients with ACC eventually develop metastases. Among all patients diagnosed with or having a history of metastatic disease in ACC-TCGA (n=40), 8/40 were COC1 (20%), 11/40 were COC2 (27.5%), and 21/40 (52.5%) were COC3.

The unique molecular features that define COC1, COC2, and COC3 classes of tumors indicate that each ACC type (COC1, COC2, COC3) will be homogeneously susceptible to an therapy, or combination of therapies, targeted for use in the specific class.

Figure 9:
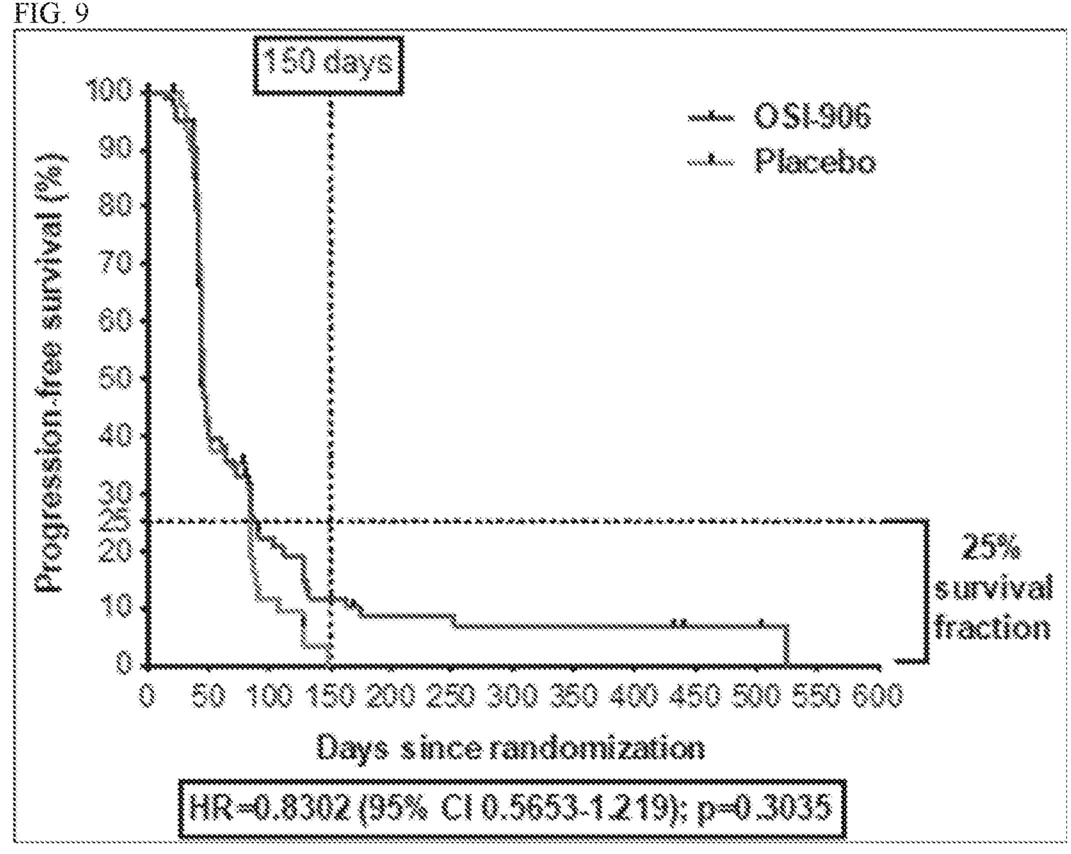
FIG. 9. Progression-free survival curve of patients enrolled in Fassnacht et al. Lancet Oncology 2015 study.

A Phase 3 study evaluating efficacy of OSI-906/linsitinib in patients with advanced adrenocortical carcinoma (ACC) is published in Fassnacht et al. *Lancet Oncology* 2015. In this trial, eligible patients were treated with OSI-906 or placebo until experiencing unacceptable adverse drug effects or a progression event, defined by RECIST criteria (Eisenhauer et al. *Cur J. Cancer.* 2009); patients who experienced unacceptable adverse drug effects or a progression event were withdrawn from the trial. Fassnacht et al. reported no statistical difference between the Kaplan-Meier progression-free survival curves of linsitinib-treated and placebo-treated patients. However, it was observed that all patients treated with placebo had disease progression by 150 days after randomization, such that, a bifurcation was observed in the disease kinetics of the linsitinib-treated versus placebo-treated groups at the 25% survival fraction, with a long progression-free survival interval (>150 days) in a subset of patients in the linsitinib treatment arm. This long progression-free survival interval was not observed in the placebo arm and is indicative of linsitinib response (FIG. 9).

The data from this study demonstrated a favorable response in 6/90 OSI-906-treated patients. This includes 4 patients who achieved a partial response (PR) by RECIST criteria (Eisenhauer et al. *Eur J. Cancer.* 2009), and 2 patients who achieved long-term stable disease (SD; also by RECIST criteria, Eisenhauer et al. *Eur J. Cancer.* 2009). These individuals are tabulated in Table 2.

TABLE 2

Responders: Patients who responded favorably to OSI-906 in Fassnacht et al. *Lancet Oncology* 2015. Grade strata were determined according to Beuschlein et al. *J Clin Endocrinol Metab* 2015 or Weiss et al. *Am J Surg Pathol* 1989.

| Patient ID | Best change from baseline in sum of target lesions (%) | Progression-free survival (days) | Best overall response | Tumor grade | Grade strata |
|---|---|---|---|---|---|
| A | −78.46153846 | 440+ | PR | Ki67 10% | Intermediate |
| B | −50 | 169+ | PR | Ki67 20% | High |
| C | −45.625 | 504+ | PR | Ki67 3% | Low |
| D | −45 | 525+ | PR | mitotic figures visible | Unknown |
| E | −5.882352941 | 205+ | SD | Unknown | Unknown |
| F | 0 | 433+ | SD | Unknown | Unknown |

After the trial ended, exome sequencing was performed on tumor DNA from 12 patients treated with OSI-906: 6 patients who responded favorably to OSI-906 (Table 2), and 6 matched non-responders (Table 3, below). Non-responders were matched on the basis of tumor grade, the gold-standard method to prognosticate and classify ACC at this time, to ensure that responder and non-responder groups were otherwise comparable. All non-responders progressed on linsitinib therapy ("PD"), as defined by RECIST criteria (Eisenhauer et al. *Eur J. Cancer.* 2009).

TABLE 3

Non-responders: Subset of patients who did not respond to OSI-906 in Fassnacht el al. *Lancet Oncology* 2015. Grade strata were determined according to Beuschlein et at. *J Clin Endocrinol Metab* 2015 or Weiss et at, *Am J Surg Pathol* 1989.

| Patient ID | Best change from baseline in sum of target lesions (%) | Progression-free survival (days) | Best overall response | Tumor grade | Grade strata |
|---|---|---|---|---|---|
| G | 23.5059761 | 42 | PD | Ki67 15% | Intermediate |
| H | 32.25806452 | 38 | PD | Ki67 15% | Intermediate |
| I | 35.29411765 | 41 | PD | mitotic figures visible | Unknown |
| J | 38.28125 | 42 | PD | Ki67 15% | Intermediate |
| K | 48.35164835 | 48 | PD | Ki67 20% | High |
| L | 58.33333333 | 42 | PD | Ki67 20% | High |

The goal of this exome sequencing study was to identify molecular predictors of responsiveness to OSI-906. Exome sequencing data was analyzed to characterize the loss of heterozygosity (LOH) profiles of each tumor. A bioinformatics pipeline (samtools mpileup, bcftools call, and R/CRAN package changepoint) was used to generate B-allele frequency profiles of each tumor and identify breakpoints between regions with variable allele frequencies.

Figure 10:
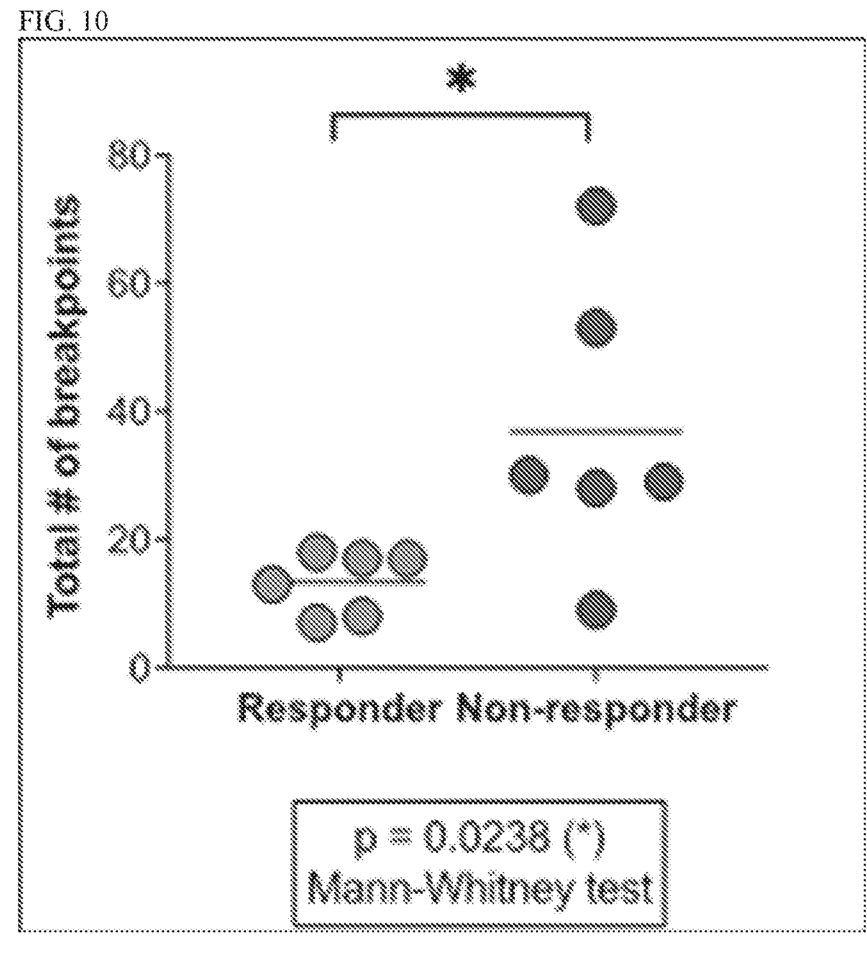
FIG. 10. Breakpoint analysis of exome sequencing data from Responders and Non-responders treated with linsitinib. Each dot in this figure represents the total number of breakpoints identified in a sequenced tumor from a patient, categorized by "Responder" or "Non-responder" status.
Figure 11:
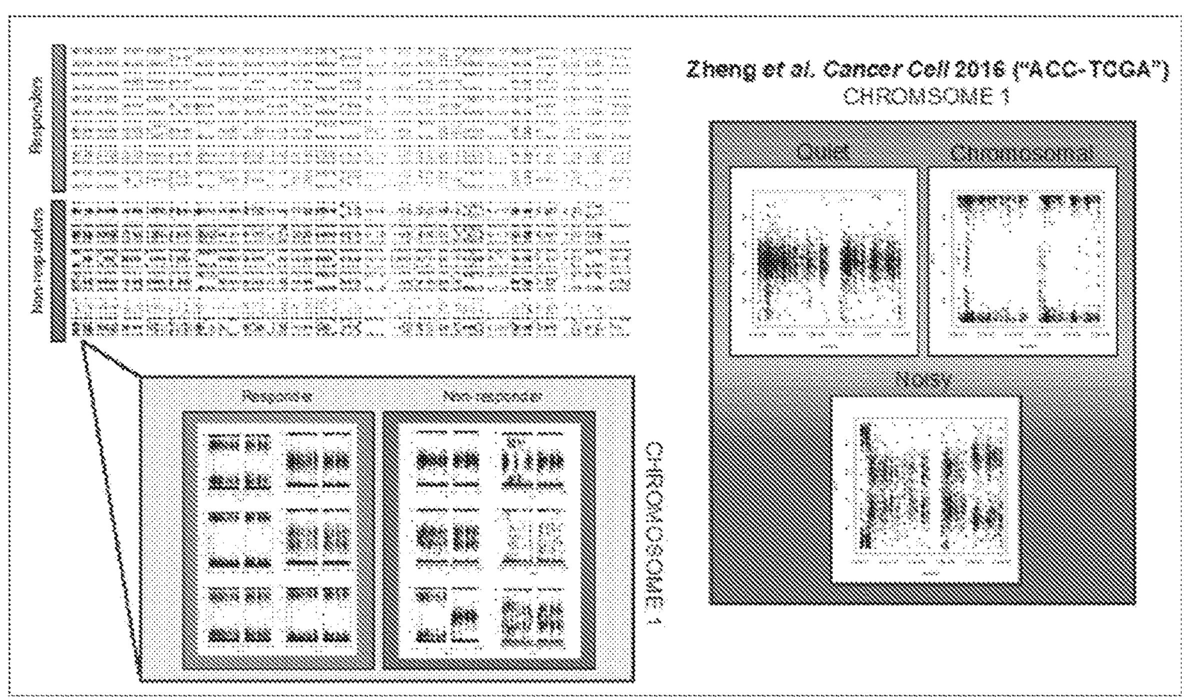
FIG. 11. Patients with noisy ACC progress on linsitinib. Left, top is depicted B-allele frequency profiles from each autosomal chromosome (columns) from each patient (rows) categorized as "Responder" or "Non-responder." Left, below zooms in on chromosome I from each patient. Right, chromosome 1 from patient samples representing each SCNA class from ACC-TCGA.

The exome sequencing revealed that linsitinib responders possess fewer chromosomal breakpoints and "Chromosomal" SCNA profile and linsitinib non-responders possess a "Noisy" SCNA profile (FIG. 10, FIG. 11). This initial step demonstrates that linsitnib responders were either COC1 or COC2, while linsitinib non-responders were COC3 (FIG. 1).

To determine whether these linsitinib responders were COC1 or COC2, as a next step the disease kinetics of patients enrolled in the original linsitinib trial were examined. It was hypothesized that, based on where the split in the survival curves of patients treated with drug or placebo was observed, it would be possible to determine which class of ACC responded to therapy.

As expected, it was determined that no patients with rapidly progressive, COC3 disease (accounting for 52.5% of all metastatic ACC) would respond to linsitinib therapy based on the molecular study above. Therefore, no divergence between the placebo and linsitinib treatment arms prior to the 47.5% survival fraction was expected, and this is what was observed.

It was further expected that if patients with COC2 disease only (accounting for 27.5% of all metastatic ACC) responded to linsitinib therapy, a divergence of the survival curves spanning the range between the 47.5% survival fraction and 20% survival fraction would be observed. However, it was instead observed that the divergence of the survival curves occurred only starting at the 25% survival fraction, as depicted in FIG. 9.

The timing of this divergence demonstrated that the patients who responded to linsitinib therapy were mostly, if not entirely, comprised of patients with COC1, the slowest growing disease subtype.

With these collective means used to identify COC1 patients (as distinct from COC2 or COC3), it was further observed, based on the divergence of the Phase 3 study survival curves, that the extent and duration of the long-term progression-free survival of the 4 of 6 COC1 patients in the linsitinib treatment arm who achieved a partial response (PR) was so far beyond the known expectations for any patient with metastatic ACC, that the response must have been due to a therapeutic drug effect, and not due simply to them having disease which was naturally more slowly progressive.

Supporting this assertion is that, in contrast, all patients the placebo arm (which included patients with COC1 tumors), who thus are a patient sample by which to demonstrate the known natural history of patients with metastatic ACC, progressed by 150 days. This result further supports the assertion that patients with intrinsically slow-growing COC1 disease, if left untreated, will still and inevitably experience a progression event by 150 days, and serves to support the conclusion that COC1 linsitinib responders were, indeed, responding to the therapeutic effect of the drug.

Example 3

Figure 12:
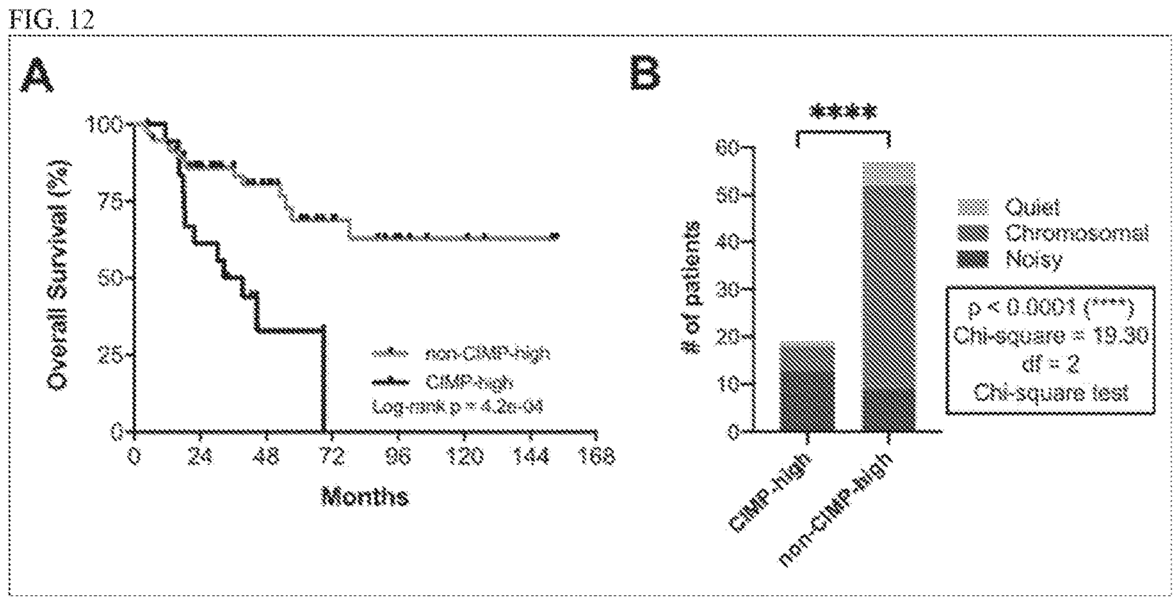
FIG. 12. Deadly CIMP-high tumors from ACC-TCGA frequently possess noisy copy number/LOH profile. A, adapted from Mohan & Lerario et al. Clinical Cancer Research 2019 shows that tumors with CIMP-high status in ACC-TCGA are routinely deadly. B, shows that CIMP-high tumors from ACC-TCGA are significantly enriched for noisy copy number/LOH profile, while non-CIMP-high tumors from ACC-TCGA are significantly enriched for chromosomal copy number/LOH profile, consistent with COC3.

Given that 6/90 patients in Fassnacht et al. 2015 responded favorably to linsitinib (Table 2, FIG. 9), the invention disclosed herein of novel molecular features attributed to linsitinib responders (FIG. 7-8), and the invention of molecular diagnostic markers which may be used to identify patients with, and without, these features (FIG. 12 and Mohan & Lerario et al. 2019), a clinical trial evaluating efficacy of linsitinib employing these molecular diagnostic markers described above is conducted.

Patients arc stratified for inclusion in a trial according to ACC-TCGA molecular classes as detailed in Table 1, to include only patients who fall into the class of COC1. The major advantage of this molecular classification strategy is that in addition to enriching for COC1 (ACC-TCGA) (Table 1; FIGS. 4-8), disease kinetics is also captured using biomarkers (Table 4, below). The presence of G0S2 methylation above a threshold (a proxy for CIMP-high DNA methylation and therefore COC3 status) is used to exclude COC3 patients. The presence of BUB1B-PINK1 below a threshold in the absence of G0S2 methylation, is used exclude COC2 patients. The presence of BUB1B-PINK1 above a threshold in the absence of G0S2 methylation, is used to identify and enroll COC1 patients. Linsitinib is given to enrolled patients as monotherapy for their cancer.

TABLE 4

Higher BUB1B-PINK1 predicts slower disease kinetics. Multivariable Cox proportional hazards model performed on BUB1B-PINK1 score from the primary tumors of patients from Mohan & Lerario et al. *Clinical Cancer Research* 2019 demonstrates that BUB1B-PINK1 remains significant and protective for death (HR <1) in multivariable models including ENSAT stage. ENSAT IV is metastatic ACC. Since metastatic ACC is routinely fatal, this demonstrates higher BUB1B-PINK1 is associated with slower disease kinetics, consistent with its ability to capture COC1 tumors.

| Variable | HR for Death | p-value | 95% CI of HR |
|---|---|---|---|
| BUB1B-PINK1 | 0.6734 | <0.0001 | 0.5742 to 0.7897 |
| ENSAT I-II | 0.0000 | 0.9697 | 2.5628E−261 to 47.8471E+249 |
| ENSAT III | 2.6672 | 0.0286 | 1.1079 to 6.4210 |
| ENSAT IV | 7.1806 | <0.0001 | 3.1270 to 16.4891 |

With the application of molecular biomarkers, 100-25.8% or 74.2% of patients with metastatic disease but are not COC1 are eliminated from trial enrollment, all of whom are unlikely to respond to IGF2/IGF1R targeting monotherapy.

In such a hypothetical clinical study, of 90 patients potentially eligible for enrollment using the criteria of the prior GALACCTIC trial in whom there were 6 responders (including, but not limited to, a history of having failed all standard of care treatments for their disease), the following results are contemplated: Application of BUB1B-PINK1 and G0S2 methylation excludes 0.742*90 patients=67 patients, leaving 23 patients enrolled into the trial. Of those 23 patients, it is contemplated that once again 6 responders to treatment are observed. As such, a response rate of 6/23 or 26% is observed, a clinically significant increase in response rate compared to the prior failed trial, for which response was 6/90=6.7%. This 26% response rate, an increase of nearly 4-fold, will serve to demonstrate and to confirm the clinical utility of the drug for the tested patient population and may be used in support of regulatory filings seeking marketing approval for linsitinib. This trial design, size and numerical degree of improved efficacy are merely exemplary, as will be appreciated by those of ordinary skill in the art, a trial of different design, size and/or statistical powering, as well as response rate results of a similarly improved nature but of different numerical value, may be used to demonstrate the clinically meaningful improvement to linsitinib response rate offered by the methods disclosed herein.

All publications and patents mentioned in the above specification are herein incorporated by reference. Various modifications and variations of the described method and system of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled in the medical sciences are intended to be within the scope of the following claims.

The invention claimed is:

1. A method for identifying a subject with adrenocortical carcinoma (ACC) as having COC1 ACC, comprising:

a) obtaining or having obtained a sample from the subject; and measuring the level of GOS2 methylation and BUB1B-PINK1 expression score in the sample;

b) identifying the subject as having COC1 ACC when the level of GOS2 methylation is less than approximately 4.696% plus or minus 1%, 5%, or 10% and the BUB1B-PINK1 expression score is greater than approximately 1.646 plus or minus 1%, 5%, or 10%; and administering linsitinib to said subject identified as having COC1 ACC.

2. The method of claim 1, wherein said threshold level of GOS2 methylation is determined using methylation-sensitive restriction digest and amplification.

3. The method of claim 1, wherein said threshold level of GOS2 methylation is determined using unsupervised complete hierarchical clustering using Euclidean distance on logit-transformed methylation beta-values.

4. The method of claim 1, wherein said biological sample is selected from the group consisting of a tissue sample, a biopsy sample, a blood sample, and a urine sample.

5. The method of claim 1, wherein said measuring the level of GOS2 methylation and BUB1B and/or PINK1 expression comprises the use of one or more reagents selected from the group consisting of a nucleic acid probe or probes that hybridizes to at least one of BUB1B, PINK1, and GOS2, one or more nucleic acid primers for the amplification or extension of at least one of BUB1B, PINK1, and GOS2, one or more methylation-specific restriction enzymes, and one or more nucleic acid primers that bind specifically to methylated GOS2 nucleic acids.

* * * * *